United States Patent
Mashal et al.

(10) Patent No.: US 12,102,759 B2
(45) Date of Patent: Oct. 1, 2024

(54) SEALING FORCE DETECTION ENABLED, THERAPEUTIC FLUID DELIVERY DEVICE

(71) Applicant: Fisher & Paykel Healthcare Limited, Auckland (NZ)

(72) Inventors: Fadi Karim Moh'd Mashal, Auckland (NZ); Matthew Roger Stephenson, Auckland (NZ); Jeroen Hammer, Auckland (NZ); Daniel John Smith, Auckland (NZ); Jonathan David Harwood, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 776 days.

(21) Appl. No.: 17/031,499

(22) Filed: Sep. 24, 2020

(65) Prior Publication Data

US 2021/0069441 A1  Mar. 11, 2021

Related U.S. Application Data

(63) Continuation of application No. 15/120,380, filed as application No. PCT/NZ2015/050020 on Feb. 26, 2015, now Pat. No. 10,814,086.

(Continued)

(51) Int. Cl.
*A61M 16/06* (2006.01)
*A61B 5/00* (2006.01)

(52) U.S. Cl.
CPC .... *A61M 16/0616* (2014.02); *A61M 16/0683* (2013.01); *A61B 5/6803* (2013.01);

(Continued)

(58) Field of Classification Search
CPC ........ A47G 9/10; A61B 5/0036; A61B 5/087; A61B 5/11; A61B 5/4812; A61B 5/4818;
(Continued)

(56) References Cited

U.S. PATENT DOCUMENTS

| | | | |
|---|---|---|---|
| 2,654,060 A | 9/1953 | Stovall, Jr. et al. | |
| 3,971,368 A * | 7/1976 | Forbes | A62B 7/00 128/201.15 |

(Continued)

FOREIGN PATENT DOCUMENTS

| | | |
|---|---|---|
| EP | 2478839 | 7/2012 |
| EP | 3033130 B1 | 10/2017 |

(Continued)

OTHER PUBLICATIONS

International Search Report for Application No. PCT/NZ2015/050020 dated Apr. 27, 2015, 5 pages.

(Continued)

*Primary Examiner* — Annette Dixon
(74) *Attorney, Agent, or Firm* — Knobbe Martens Olson & Bear LLP

(57) ABSTRACT

A respiratory mask can include one or a plurality of force sensors configured to detect a force imparted to a user's skin. Output from the one or more sensors can be represented in a way useful to the patient or healthcare provider for adjusting the mask to achieve a desired fitment. A representation of the detected forces can be displayed on a separate display device or on the mask.

21 Claims, 24 Drawing Sheets

Related U.S. Application Data

(60) Provisional application No. 61/945,001, filed on Feb. 26, 2014.

(52) U.S. Cl.
CPC ...... *A61B 5/6843* (2013.01); *A61M 2205/332* (2013.01); *A61M 2205/35* (2013.01); *A61M 2205/502* (2013.01)

(58) Field of Classification Search
CPC ..... A61B 5/6803; A61B 5/6843; A61B 7/003; A61B 7/04; A61F 5/56; A61G 7/05769; A61G 7/072; A61H 2201/501; A61H 2205/12; A61H 2230/25; A61H 2230/65; A61H 9/0078; A61M 11/02; A61M 15/0086; A61M 15/009; A61M 16/0003; A61M 16/0051; A61M 16/0063; A61M 16/0066; A61M 16/0069; A61M 16/01; A61M 16/021; A61M 16/022; A61M 16/024; A61M 16/04; A61M 16/0434; A61M 16/044; A61M 16/06; A61M 16/0605; A61M 16/0616; A61M 16/0622; A61M 16/0633; A61M 16/0683; A61M 16/0816; A61M 16/0841; A61M 16/0875; A61M 16/109; A61M 16/1095; A61M 16/16; A61M 16/161; A61M 16/20; A61M 16/201; A61M 16/202; A61M 2016/0027; A61M 2016/0033; A61M 2016/0036; A61M 2016/0039; A61M 2016/1025; A61M 2021/0027; A61M 2021/0044; A61M 2021/005; A61M 2039/1005; A61M 21/00; A61M 21/02; A61M 2202/0085; A61M 2202/0208; A61M 2202/0225; A61M 2205/0294; A61M 2205/13; A61M 2205/15; A61M 2205/18; A61M 2205/33; A61M 2205/3303; A61M 2205/3306; A61M 2205/332; A61M 2205/3331; A61M 2205/3344; A61M 2205/3368; A61M 2205/3375; A61M 2205/35; A61M 2205/3561; A61M 2205/3569; A61M 2205/3584; A61M 2205/3592; A61M 2205/3606; A61M 2205/43; A61M 2205/50; A61M 2205/502; A61M 2205/505; A61M 2205/52; A61M 2205/581; A61M 2205/583; A61M 2205/587; A61M 2205/59; A61M 2205/6045; A61M 2205/6054; A61M 2205/6072; A61M 2205/70; A61M 2205/8206; A61M 2209/088; A61M 2210/0662; A61M 2210/1032; A61M 2230/04; A61M 2230/10; A61M 2230/14; A61M 2230/205; A61M 2230/30; A61M 2230/40; A61M 2230/43; A61M 2230/432; A61M 2230/50; A61M 2230/60; A61M 2230/63; A61M 2230/65; A61M 25/10; A61M 25/1018; A61M 25/10184; A61M 25/10185; A61M 25/10186; A61N 1/40; Y10S 128/908; Y10S 128/925
See application file for complete search history.

(56) References Cited

U.S. PATENT DOCUMENTS

| | | | | |
|---|---|---|---|---|
| 4,166,465 | A | * | 9/1979 | Esty ........................ A61B 18/16 607/152 |
| 6,147,547 | A | * | 11/2000 | Ogura .................... H02M 3/073 327/390 |
| 6,240,921 | B1 | * | 6/2001 | Brydon ............... A61M 16/024 128/205.25 |
| 6,349,724 | B1 | * | 2/2002 | Burton ................... F04D 29/052 128/204.22 |
| 9,114,223 | B2 | | 8/2015 | Sofranko et al. |
| 9,687,619 | B2 | | 6/2017 | Stuebiger et al. |
| 9,687,624 | B2 | * | 6/2017 | Haas ................. A61M 16/0633 |
| 10,350,375 | B2 | * | 7/2019 | Hickey ............. A61M 16/0051 |
| 10,814,086 | B2 | | 10/2020 | Mashal et al. |
| 11,278,690 | B2 | * | 3/2022 | Hickey ................. A61M 16/06 |
| 2004/0163648 | A1 | * | 8/2004 | Burton .............. A61M 16/0694 128/204.21 |
| 2008/0083412 | A1 | | 4/2008 | Henry et al. |
| 2011/0263950 | A1 | | 10/2011 | Larson |
| 2011/0029715 | A1 | | 12/2011 | Wallnewitz |
| 2012/0190998 | A1 | | 7/2012 | Armitstead et al. |
| 2012/0199131 | A1 | * | 8/2012 | Sofranko .............. A61M 16/06 128/206.21 |
| 2012/0296191 | A1 | | 11/2012 | McGrath |
| 2013/0180523 | A1 | | 7/2013 | Huggins |
| 2015/0224275 | A1 | | 8/2015 | Pastoor et al. |
| 2016/0184538 | A1 | * | 6/2016 | Grashow ........... A61M 16/0051 128/202.22 |
| 2016/0279359 | A1 | * | 9/2016 | Chang ................... A61M 16/06 |
| 2017/0065784 | A1 | | 3/2017 | Marshal et al. |
| 2017/0361045 | A1 | * | 12/2017 | Fu ..................... A61M 16/0633 |
| 2022/0387740 | A1 | * | 12/2022 | Fu ..................... A61M 16/0051 |

FOREIGN PATENT DOCUMENTS

| | | |
|---|---|---|
| WO | WO 2013/183018 | 12/2013 |
| WO | WO 2014/024086 A1 | 2/2014 |
| WO | WO 2015/002652 | 1/2015 |
| WO | WO 2015/022595 A1 | 2/2015 |
| WO | WO 2015/130180 | 9/2015 |

OTHER PUBLICATIONS

GB Examination Report for Application No. GB1713996 dated Nov. 28, 2017; 5 pages.
GB Examination Report for Application No. GB1713995 dated Nov. 27, 2017; 5 pages.
Australian Examination Report for Application No. 2015223574 dated Nov. 20, 2018; 4 pages.
Australian Examination Report for Application No. 2020200956 dated Jul. 20, 2020; 4 pages.

* cited by examiner

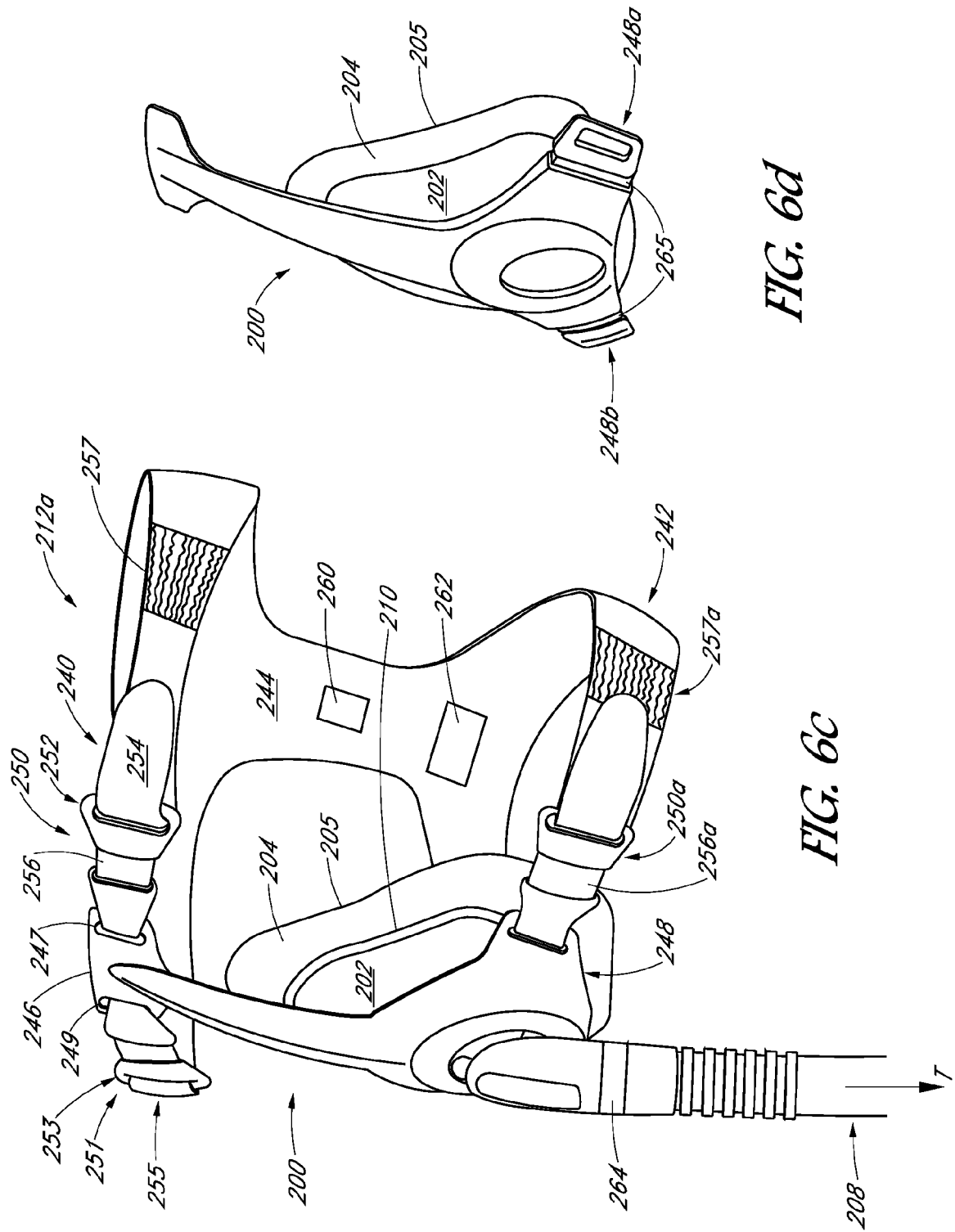

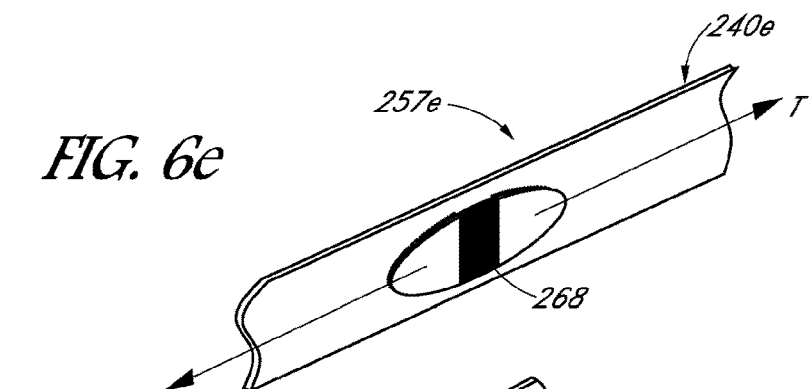
FIG. 6e
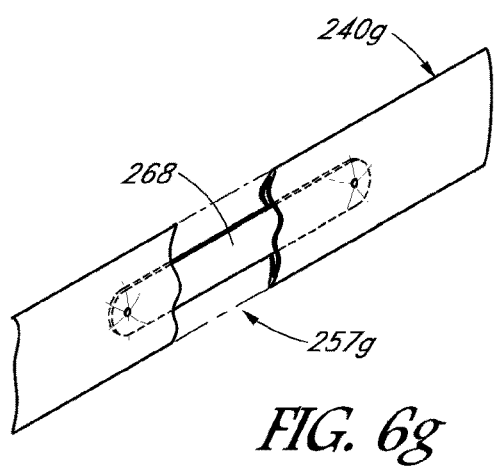
FIG. 6f
FIG. 6g
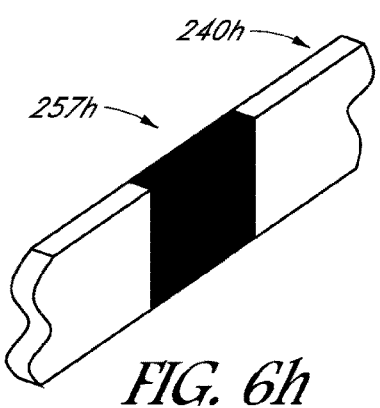
FIG. 6h
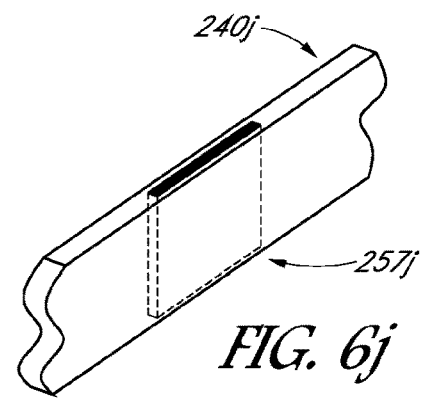
FIG. 6j
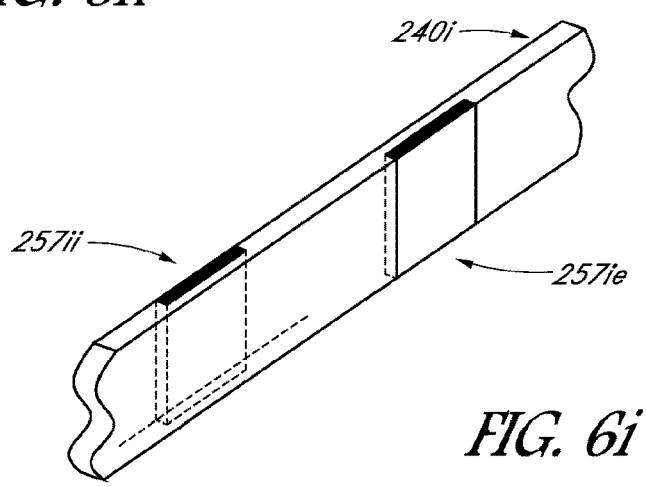
FIG. 6i

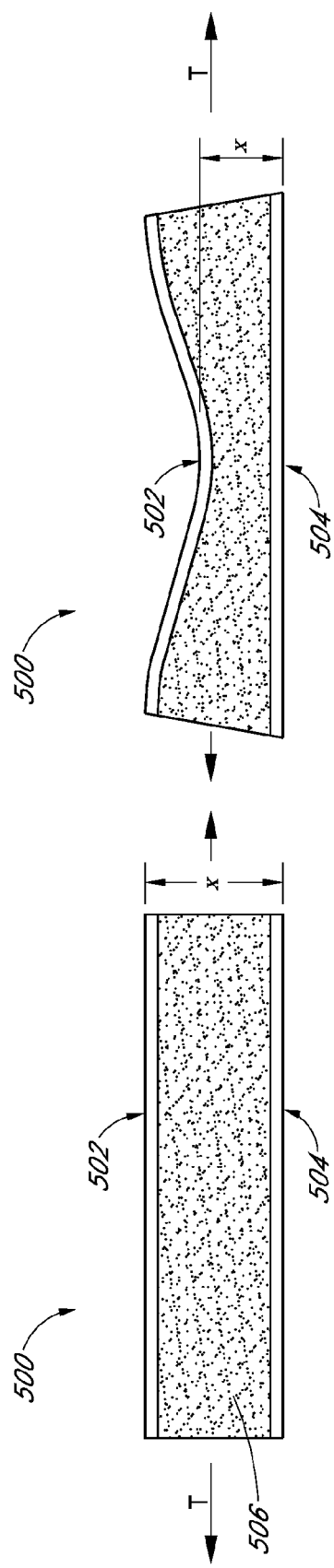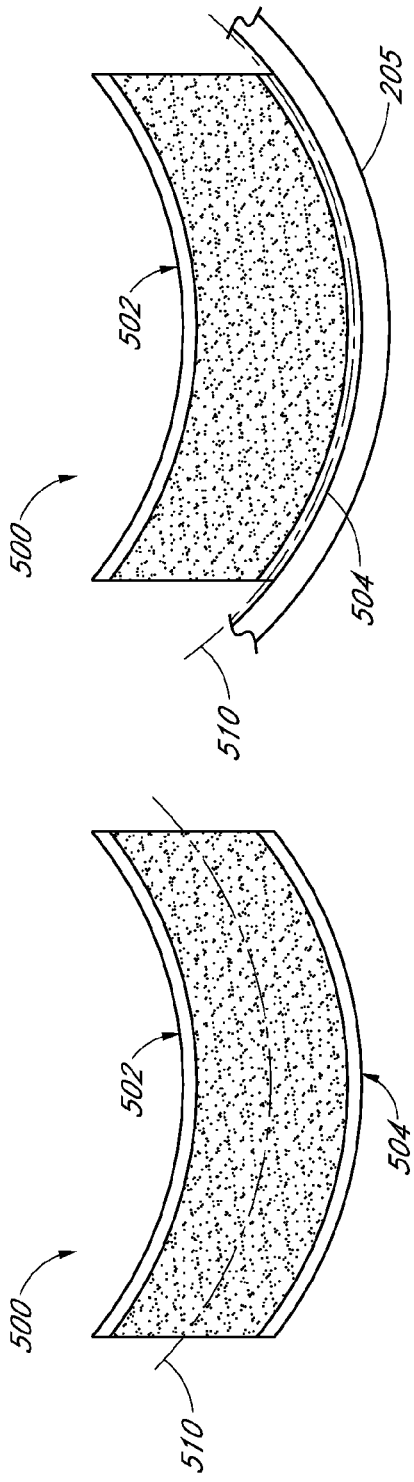

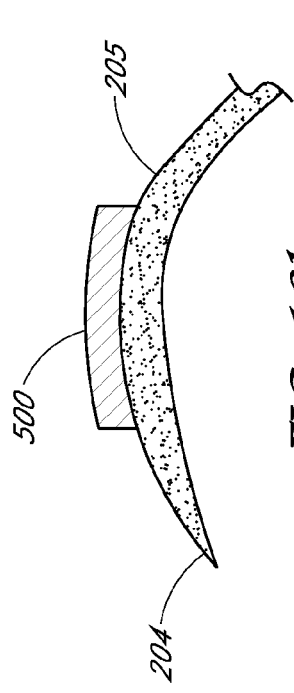
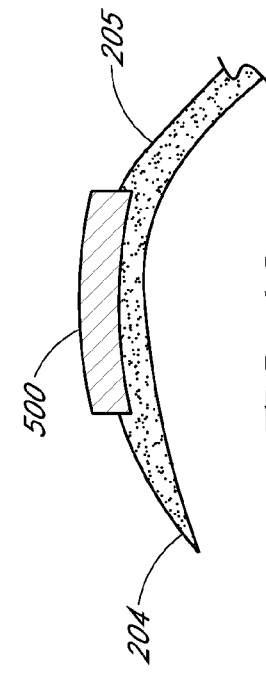
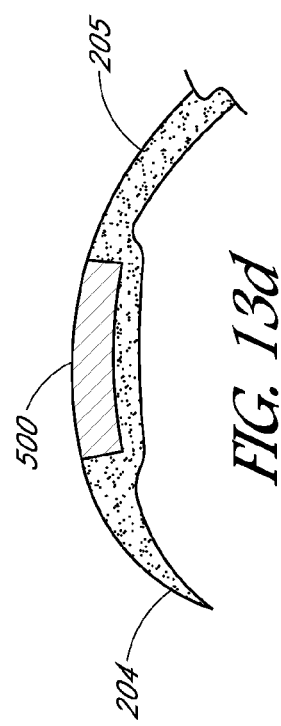
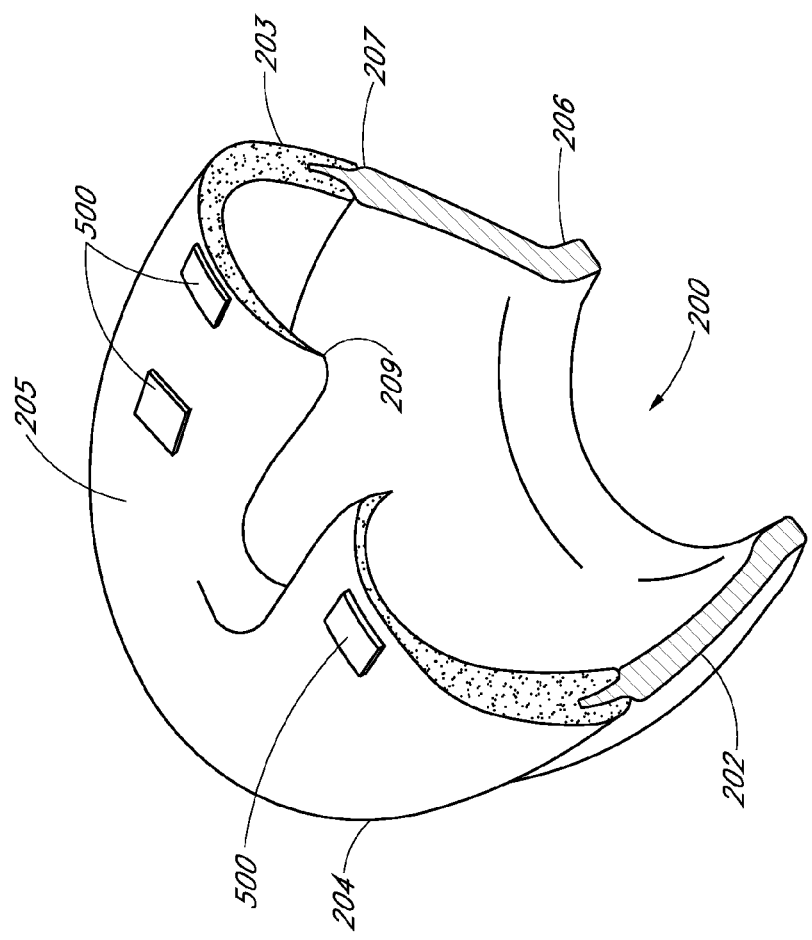

SEALING FORCE DETECTION ENABLED, THERAPEUTIC FLUID DELIVERY DEVICE

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

TECHNICAL FIELD

The present embodiments relate to therapeutic fluid delivery devices, including, for example, therapeutic masks with sealing force detection.

BACKGROUND

Fluid delivery devices which include a sealing device providing a seal with a patient's skin, often in the form of a butting seal, are used for a variety of different therapies. Some of this type of therapeutic fluid delivery devices are designed for delivering breathable gasses, for example, including but not limited to non-invasive ventilation, oxygen therapy and continuous positive airway pressure (CPAP), for the treatment of various respiratory conditions. Many of these respiratory therapies are better administered and more effective when a substantially airtight seal is achieved between the mask and the user.

The contours of different patient's skin vary, and thus, fluid delivery devices are typically made to fit a variety of differently-shaped faces. However, due to the range of differing anatomical geometries in the human population, it can be difficult to achieve a desired seal on every patient. This is especially true in the context of fluid delivery devices in the form of respiratory masks; a result of the variability of the geometry of different patient's faces in the areas surrounding the nose and/or mouth.

In the context of respiratory masks, it is common to apply substantial forces to a mask and user's face in an attempt to overcome sealing challenges presented by the depth and variation of facial contours, for example, in the areas around the bridge of the nose. The application of forces to a mask and thus a user's face can cause discomfort as well as injuries to the user and is not always successful at attaining satisfactory leak rates.

For example, FIGS. 1 and 2 illustrate skin sores caused by existing respiratory masks. In some cases, the patient is not conscious or lucid and thus not able to indicate discomfort or pain that may precede such injuries.

SUMMARY OF THE INVENTION

It is an object of the present invention to provide a therapeutic fluid delivery devices, including, for example, therapeutic masks with sealing force detection, that will at least go some way towards improving on the above or which will at least provide the public or the medical profession with a useful choice.

An aspect of at least one of the embodiments disclosed herein includes the realization that patient comfort can be improved and patient injuries caused by masks can be reduced by providing for the detection and display of forces imparted onto a patient's skin at the location of the seal of the mask. For example, by detecting the forces imparted onto a patient's face at the seal of a mask, then displaying a representation of the detected force, a patient or healthcare provider can identify whether a mask has been applied in a non-optimal manner, then adjust the mask to correct the application of the mask.

This can provide significant benefits with regard to the use of various kinds of masks, including reducing the number of leaks and/or the leak rate to acceptable magnitudes or eliminate leaks altogether. Such mask features can also reduce forces on the user's skin ("skin pressure"), in particular, areas of the face where the skin is thin such as the nasal bridge, for example. Additionally, force detection can lead to a determination that a particular mask cannot be adjusted to produce a desired leak rate without using excessive application force, and thus, different mask should be considered.

Designing such masks presents several challenges, including accommodating differently sized and shaped faces, as well as minimizing the force of contact between the seal and the corresponding portions of each different user's face. Ideally, a mask will not leak with very low skin pressure. Leaks will occur, however, where the skin pressure is insufficient to counter the gaseous pressure differential between the inside and outside of the mask. Thus, when unacceptable leaking is found using a typical mask, the force on the entire mask (e.g., by way of a strap) is typically increased until leaks are reduced to an acceptable level or eliminated. However, such additional force also increases the force of contact between the seal and the user's face (skin pressure) at locations where no leaking occurred, thereby generating unnecessarily higher forces at some locations, which can cause discomfort and/or injury.

FIGS. 1 and 2 schematically illustrate facial skin injuries suffered by patients who wore respiratory masks while receiving medical care. FIG. 1 illustrates a more generalized, inverted U-shaped injury 10 extending from the patient's cheeks and up and over the bridge of the nose. As shown in FIG. 1, the injury 10 includes larger regions 12, 14 lower down on the user's face and another larger portion 16 on the bridge of the patient's nose (e.g., the nose bridge injury area 16). Additionally, there are thinner, smaller regions 18, 20 lower down on the user's face, between the nose bridge injury area 16 and the lower larger portions 12, 14. As such, it appears that the mask causing this injury generated uneven forces around the patient's cheeks and nose bridge.

FIG. 2 illustrates a highly localized injury 22 appearing only on the bridge of the nose of the patient. More severe injuries, such as that illustrated in FIG. 2, are more common in areas of the face where the skin is thin, i.e. where bone is close to skin i.e. the nasal bridge. These are the areas of the face that experience the highest loads due to over tightening the headgear straps of the mask system. Excessive skin pressure can restrict blood flow, thereby starving the skin tissue of oxygen and nutrients and accelerating breakdown of the skin tissue.

An aspect of at least one of the embodiments disclosed herein includes the realization that misapplication of a mask, which may cause leaks, injury, or discomfort, can be due to a misalignment of the mask with the patient's face, characterized by excessive, non-uniform pressure along the seal-skin contact area.

In this context, an "optimal" alignment or fitment of a mask with a user's face would be the alignment and strap tension that results in an acceptable leak rate or no leak, where the skin pressure exerted on the patient's face along the sealing surface of the mask is the most uniform and at the lowest magnitude. However, detecting nonuniformity of the skin pressure is difficult for a patient to sense and resolve when applying a mask to their own face. Additionally, a healthcare provider cannot perceive the skin pressure when applying a mask to a patient, particularly when the patient is unconscious or not sufficiently lucid to assist.

Thus, in accordance with an embodiment, a therapeutic fluid delivery device includes a seal and is configured to detect a force between the seal and a target area of a patient's body. The seal portion can comprise a sealing surface configured to form a seal with a patient's skin along a perimeter encircling the target area of the patient. The fluid delivery device can also include at least a plurality of sensors configured to detect a force imparted to the patient's skin by the sealing surface.

By including at least a plurality of sensors, a force differential can be determined. For example, where the force of one sensor is greater than the force detected by the other sensor, a force nonuniformity is detected. A patient or healthcare provider could use the detection of such a non-uniformity as a guide to adjusting the fluid delivery device to achieve a better fitment.

Thus, in accordance with another embodiment, a mask can include a seal portion and can be configured to detect a force between the seal portion and an area of the patient's skin encircling at least one respiratory orifice of a patient. The seal portion can comprise a sealing surface configured to form a seal with a patient's skin along a perimeter encircling the at least one respiratory orifice. The mask can also include at least a plurality of sensors configured to detect a force imparted to the patient's skin by the sealing surface.

In accordance with another embodiment, a respiratory mask fitment system can include a mask including a seal portion comprising a sealing surface configured to form a seal with the skin of a human face along the perimeter encircling at least one respiratory orifice of the patient. A first sensor can be configured to detect a first force applied to the seal portion and to output a first data indicative of the force detected by the sensor. A display system including a display device can be connected to the sensor and configured to display a representation of the first data.

By providing a system that can display a representation indicative of pressure exerted by a mask seal against the face of a patient, the patient or healthcare provider can observe the force detected and use that information for achieving a better fitment of the mask.

In accordance with another embodiment, a method of fitting a mask on a patient can include placing a mask having a seal portion over a respiratory orifice of a patient. The method can also include detecting a force imparted to the seal portion at a first location and displaying a representation of the force on a display device. The method can also include adjusting the mask based on the displayed force.

In some configurations, a respiratory mask includes a seal and is configured to detect a force between the seal and a human face. The mask can comprise a seal portion comprising a sealing surface configured to form a seal with face along a perimeter encircling at least one respiratory orifice of a human. A plurality of sensors can be configured to detect a force applied to the seal portion.

In some configurations, the plurality of elastic sensors comprises at least a first sensor configured to detect a force at a first location on the seal portion, and a second sensor configured to detect a force at a second location on the seal portion different than the first location.

In some configurations, the plurality of sensors are configured to detect forces applied by the sealing surface to a portion of the human face and/or head.

In some configurations, the seal portion further comprises a cushion, the plurality of sensors being configured to detect compression of the cushion.

In some configurations, the plurality of sensors are configured to output signals indicative of force applied to the seal portion caused by deformation of the sensors.

In some configurations, the plurality of sensors are configured to detect deformation of the sensors and to output signals in response to the deformation.

In some configurations, a display system includes a display device configured to display representations of the forces detected by the plurality of sensors.

In some configurations, the display system is configured to display the representations of forces detected by the plurality of sensors and a graphical representation of the seal portion.

In some configurations, the display system is configured to display the graphical representation of the seal portion corresponding to a front elevational view of the mask.

In some configurations, the display system is configured to display the graphical representation of the seal portion corresponding to a rear elevational view of the mask.

In some configurations, the display system is configured to display data indicative of magnitudes forces detected by the plurality of sensors in real time.

In some configurations, the display device is disposed on the mask.

In some configurations, the display device comprises a plurality of lights positioned proximate to the plurality of sensors, respectively.

In some configurations, a recording device is configured to store output from the plurality of sensors.

In some configurations, the plurality of sensors comprise elastic capacitive sensors.

In some configurations, the plurality of sensors comprise layered capacitive sensors.

In some configurations, the plurality of sensors comprise a first longitudinal layer including a first electrode and second and third transverse layers including second and third electrodes overlapping the first electrode, wherein the first and second electrodes form a first capacitive sensor and the first and third electrodes for a second capacitive sensor.

In some configurations, one of the plurality of sensors comprise layered first, second, and third electrodes, the first and second electrode forming a first pair of electrodes with a first capacitance and the second and third electrodes forming a second pair of electrodes with a second capacitance.

In some configurations, the plurality of sensors comprise a first force sensor disposed on an outer side of the sealing surface and a second force sensor disposed on an inner side of the sealing surface.

In some configurations, the plurality of sensors comprise a first row of force sensors extending along a longitudinal direction of the seal portion and a second row of force sensors extending parallel to the first row.

In some configurations, a first of the plurality of sensors comprises first and second electrodes spaced apart by a dielectric layer, the first electrode comprising conductive silicone.

In some configurations, at least a first of the plurality of sensors comprises first and second electrodes spaced apart by a dielectric layer, the dielectric layer comprising silicone.

In some configurations, at least a first of the plurality of sensors comprises first and second electrodes spaced apart by a dielectric layer, wherein at least one of the dielectric layer and the first and second electrodes comprises silicone, and wherein the seal portion comprises silicone.

In some configurations, the seal portion being mounted to a frame portion, wherein at least a first of the plurality of sensors is disposed between the seal portion and the frame portion.

In some configurations, the plurality of sensors are positioned to detect forces proximate to a bridge of a human nose during use.

In some configurations, at least one of the plurality of sensors is positioned to detect a force proximate to a chin of a human during use.

In some configurations, a display system can include a display device configured to display representations of the forces detected by the plurality of sensors.

In some configurations, a respiratory mask fitment system can comprise a mask including a seal portion comprising a sealing surface configured to form a seal with skin of a human face along a perimeter encircling at least one respiratory orifice of a human. A first elastic sensor can be configured to detect a first force applied to the seal portion and to output first data indicative of a force detected by the sensor. Additionally, a display system can include a display device, the display system being connected to the first sensor and configured to display a first representation of the first data.

In some configurations, a second sensor can be configured to detect a second force applied to the seal portion and to output second data indicative of a second force detected by the second sensor, wherein the first sensor is configured to detect a force at a first location on the seal portion, and a second sensor configured to detect a force at a second location on the seal portion different than the first location.

In some configurations, the device is configured to display the pressures detected by the plurality of sensors and a graphical representation of the seal portion.

In some configurations, the display system is configured to display the graphical representation of the seal portion corresponding to a front elevational view of the mask.

In some configurations, the display system is configured to display the graphical representation of the seal portion corresponding to a rear elevational view of the mask.

In some configurations, the display system is configured to display data indicative of magnitudes forces detected by the first sensor in real time.

In some configurations, the display device is disposed on the mask.

In some configurations, a memory device can be configured to record output from the first elastic sensor.

In some configurations, the display device is connected to the first sensor wirelessly.

In some configurations, the first sensor comprises a layered capacitive sensor.

In some configurations, the first sensor comprises a first longitudinal layer including a first electrode and second and third transverse layers including second and third electrodes overlapping the first electrode, wherein the first and second electrodes form a first capacitive sensor and the first and third electrodes for a second capacitive sensor.

In some configurations, first and second force sensors can be aligned with each other.

In some configurations, the first force sensor is disposed on an outer side of the sealing surface and the second force sensor is disposed on an inner side of the sealing surface.

In some configurations, a first row of force sensors can include the first sensor and can extend along a longitudinal direction of the seal portion with a second row of force sensors extending parallel to the first row.

In some configurations, the first force sensor comprises first and second electrodes spaced apart by a dielectric layer, the first electrode comprising conductive silicone.

In some configurations, the first force sensor comprises first and second electrodes spaced apart by a dielectric layer, the dielectric layer comprising silicone.

In some configurations, the seal portion can be mounted to the frame portion, wherein the first sensor is disposed between the seal portion and the frame portion.

In some configurations, the display device comprises a first light.

In some configurations, the first light is positioned proximate to the first sensor.

In some configurations, a second sensor can be configured to detect a force on the seal portion and a second light.

In some configurations, the first sensor comprises layered first, second, and third electrodes, the first and second electrode forming a first pair of electrodes with a first capacitance and the second and third electrodes forming a second pair of electrodes with a second capacitance.

In some configurations, the seal portion comprises a right-side configured to seal against a right side of a patient's face and a left side configured to seal against a left side of a patient's face, the first and second rows of sensors being disposed on the right side of the seal portion.

In some configurations, the first force sensor comprises first and second electrodes spaced apart by a dielectric layer, wherein at least one of the dielectric layer and the first and second electrodes comprises silicone, and wherein the seal portion comprises silicone.

In some configurations, a method of fitting a mask on a patient can comprise placing a mask having a seal portion over a respiratory orifice of a patient, detecting a first force imparted to the seal portion at a first location based on deformation of the seal portion, displaying a first representation of the first force on a display device, and adjusting the mask.

In some configurations, the method also includes detecting a second force on the seal portion at a second location.

In some configurations, displaying a first representation comprises displaying a graphical representation of the mask and displaying the first representation on the graphical representation.

In some configurations, adjusting the mask comprises tightening or loosening at least one strap holding the mask on the patient.

In some configurations, the method can also include detecting at least second and third forces imparted to second and third locations on the seal portion, the first, second and third locations being proximate to a bridge of a patient's nose.

In some configurations, at least one of the first and second locations are proximate to a chin of a patient.

In some configurations, the method can also include detecting forces at a plurality of additional locations, the first location and additional locations forming an array of approximately evenly-spaced locations encircling the respiratory orifice.

In some configurations, the method can also include displaying a second representation of the second force.

In some configurations, adjusting the mask comprises changing a shape of the mask.

In some configurations, a respiratory mask can include a seal for sealing with a human face and can comprise a seal portion comprising a sealing surface configured to form a seal along a perimeter encircling at least one respiratory orifice of a human. A head strap assembly can be configured to secure the seal portion in contact with the perimeter, and at least one elastic sensor can be configured to detect a force in the head strap assembly.

In some configurations, the at least one elastic sensor is configured to detect a tension in the head strap assembly.

In some configurations, the head strap assembly comprises a plurality of strap members, the at least one elastic sensor being integrated into one of the plurality of strap members.

In some configurations, at least one elastic force sensor can be configured to detect a force applied to the seal portion.

In some configurations, at least a second elastic sensor can be configured to detect a force in the head strap assembly.

In some configurations, the head strap assembly comprises a first clip connecting first and second portions of the head strap assembly, wherein the at least one elastic sensor is incorporated into the clip.

In some configurations, the first clip comprises a first end connected to the first portion of the head strap assembly and a second end connected to the second portion of the head strap assembly, the at least one elastic sensor being connected between the first and second ends such that the at least one elastic sensor is stretched when the first and second ends are pulled away from each other by the first and second portions of the head strap assembly.

In some configurations, the first clip is removable from the head strap assembly.

In some configurations, the first clip comprises a sensor module connected to the first elastic sensor, the sensor module comprising a sensor driver, a power supply, and a wireless communication device configured to wirelessly transmit a signal indicative of an output of the at least one elastic sensor.

In some configurations, a respiratory mask assembly can have a mask portion and head strap assembly and can comprise a mask portion comprising a sealing surface configured to form a seal along a perimeter encircling at least one respiratory orifice of a human, a head strap assembly configured to secure the mask portion in a position over the at least one respiratory orifice, a first plurality of elastic sensors configured to detect forces in the head strap assembly, respectively, and a second plurality of elastic sensors configured to detect forces in the mask portion.

In some configurations, the second plurality of elastic sensors are configured to detect deformation of the sealing surface.

In some configurations, the mask portion comprises a cushion portion disposed adjacent to the sealing surface, the second plurality of elastic sensors being configured to detect deformation of the cushion portion.

In some configurations, a therapeutic fluid delivery device having a seal and configured to detect a force between the seal and a patient can comprise a seal portion comprising an outer sealing surface configured to form a seal with an area of a patient's skin encircling at least one target area of a patient, and at least a first elastic capacitive sensor configured to output a signal in response to a force imparted to the outer sealing surface.

In some configurations, the first elastic capacitive sensor is configured to output signals indicative of a range of force magnitudes imparted to the outer sealing surface.

In some configurations, the first elastic capacitive sensor is configured to output signals in a predetermined proportional relationship with the range of force magnitudes imparted to the outer sealing surface.

In some configurations, the first elastic capacitive sensor can be configured to detect a force at a first location on the sealing surface, and a second sensor can be configured to detect a force at a second location on the sealing surface spaced from the first location.

In some configurations, the seal portion is configured to extend around at least one respiratory orifice of a patient and the first elastic capacitive sensor is configured to detect forces between the sealing surface and the skin of a human face.

In some configurations, the seal portion further comprises a cushion layer disposed inwardly from the sealing surface, the first elastic capacitive sensor being embedded in the cushion layer.

In some configurations, first and second first elastic capacitive sensors can be positioned to detect forces proximate to a bridge of a human nose during use.

In some configurations, at least one of first and second elastic capacitive sensors are positioned to detect a force proximate to a chin of a human during use.

In some configurations, a display system can include a display device configured to display representations of the forces detected by the first elastic capacitive sensor.

In some configurations, the display system is configured to display forces detected by the first elastic capacitive sensor and a graphical representation of the seal portion.

In some configurations, the display system is configured to display the graphical representation of the seal portion corresponding to a front elevational view of the mask.

In some configurations, the display system is configured to display the graphical representation of the seal portion corresponding to a rear elevational view of the mask.

In some configurations, the display system is configured to display data indicative of magnitudes forces detected by the first elastic capacitive sensor in real time.

In some configurations, the display device is disposed on the mask.

In some configurations, the display device comprises a plurality of lights.

In some configurations, at least a second sensor can be configured to output a signal in response to a force imparted to the outer sealing surface, wherein the plurality of lights are positioned proximate to the first and second sensors, respectively.

In some configurations, the first sensor comprises a layered capacitive sensor.

In some configurations, the first sensor comprises a first longitudinal layer including a first electrode and second and third transverse layers including second and third electrodes overlapping the first electrode, wherein the first and second electrodes form a first capacitive sensor and the first and third electrodes for a second capacitive sensor.

In some configurations, the first sensor comprises layered first, second, and third electrodes, the first and second electrode forming a first pair of electrodes with a first capacitance and the second and third electrodes forming a second pair of electrodes with a second capacitance.

In some configurations, first and second force sensors can be aligned with each other.

In some configurations, the first force sensor is disposed on an outer side of the sealing surface and the second force sensor is disposed on an inner side of the sealing surface.

In some configurations, a first row of force sensors including the first sensor, extends along a longitudinal direction of the seal portion and a second row of force sensors extends parallel to the first row.

In some configurations, the seal portion comprises a right-side configured to seal against a right side of a patient's face and a left side configured to seal against a left side of a patient's face, the first and second rows of sensors being disposed on the right side of the seal portion.

In some configurations, the first force sensor comprises first and second electrodes spaced apart by a dielectric layer, the first electrode comprising conductive silicone.

In some configurations, the first force sensor comprises first and second electrodes spaced apart by a dielectric layer, the dielectric layer comprising silicone.

In some configurations, the first force sensor comprises first and second electrodes spaced apart by a dielectric layer, wherein at least one of the dielectric layer and the first and second electrodes comprises silicone, and wherein the seal portion comprises silicone.

In some configurations, the seal portion can be mounted to a frame portion, wherein the first sensor is disposed between the seal portion and the frame portion.

The term "comprising" is used in the specification and claims, means "consisting at least in part of". When interpreting a statement in this specification and claims that includes "comprising", features other than that or those prefaced by the term may also be present. Related terms such as "comprise" and "comprises" are to be interpreted in the same manner.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

BRIEF DESCRIPTION OF THE DRAWINGS

FIG. 6b is a perspective view of a modification of the mask illustrated in FIG. 6a.

FIG. 6c is a perspective view of a modification of the mask and head strap assembly of FIG. 4, including optional sensors at various locations on the head strap assembly.

FIG. 6d is a perspective view of a modification of the frame and seal assembly of the mask of FIG. 6c, including optional sensors.

FIG. 6e is an enlarged view of a portion of the head strap assembly of the mask of FIG. 6c illustrating an optional removable sensor assembly.

FIG. 6f is an enlarged perspective and exploded view of an optional technique for using the sensor assembly illustrated in FIG. 6d.

FIG. 6g is an enlarged perspective and partial cut-away view of an optional structural for mounting a sensor in the head strap of the mask of FIG. 6c.

FIG. 6h is an enlarged perspective view of an optional mounting arrangement of a sensor with the head strap of the mask of FIG. 6c.

FIG. 6i is an enlarged perspective view of two alternative mounting locations for a sensor on the head strap of the mask of FIG. 6c.

FIG. 6j is an enlarged perspective of an optional arrangement for mounting a sensor to the head strap with the sensor being disposed between outer layers of a head strap.

FIG. 11 is a sectional view of an elastic capacitive sensor, in a neutral state, that can be used with any of the masks of FIGS. 3-12.

FIG. 12 is a sectional view of the sensor of FIG. 11 in a deformed state.

FIG. 12a is a further sectional view of the sensor of FIG. 11 bent in a neutral state, prior to connection to another surface.

FIG. 12b is a further sectional view of the sensor of FIG. 11, bent and connected to another surface.

FIG. 13a is a schematic, perspective and sectional view of a portion of the mask of FIG. 4 illustrating optional external sensor mounting locations on the mask.

FIG. 13b is a schematic, enlarged sectional view of the mask of 13a illustrating an external mounting arrangement for a sensor.

FIG. 13c is an enlarged sectional view of the mask of FIG. 13a illustrating a partially embedded external mounting arrangement for the sensor.

FIG. 13d is an enlarged sectional view of the mask of FIG. 13a illustrating a flush, external mounting arrangement for the sensor.

FIG. 14d is an enlarged cross-sectional view of a frame-seal interface mounting arrangement for a sensor that can be used in the mask of FIG. 14a.

DETAILED DESCRIPTION

The embodiments described below are described in the context of therapeutic fluid delivery devices which include seals designed to form seals with areas of patients encircling a target treatment area. However, the inventions disclosed herein can be applied to other devices designed for uses in other environments, including devices for non-medical uses, and uses on non-humans, and/or inanimate objects.

Figure 1:
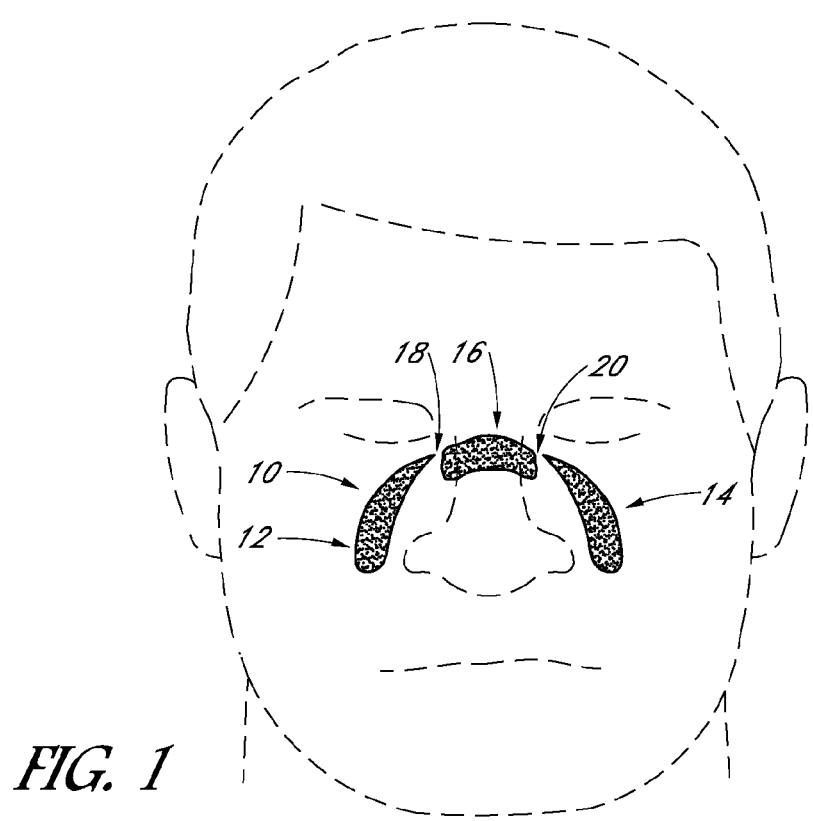
FIGS. 1 and 2 are schematic front elevational views of a patient's face showing injuries caused by known masks.
Figure 2:
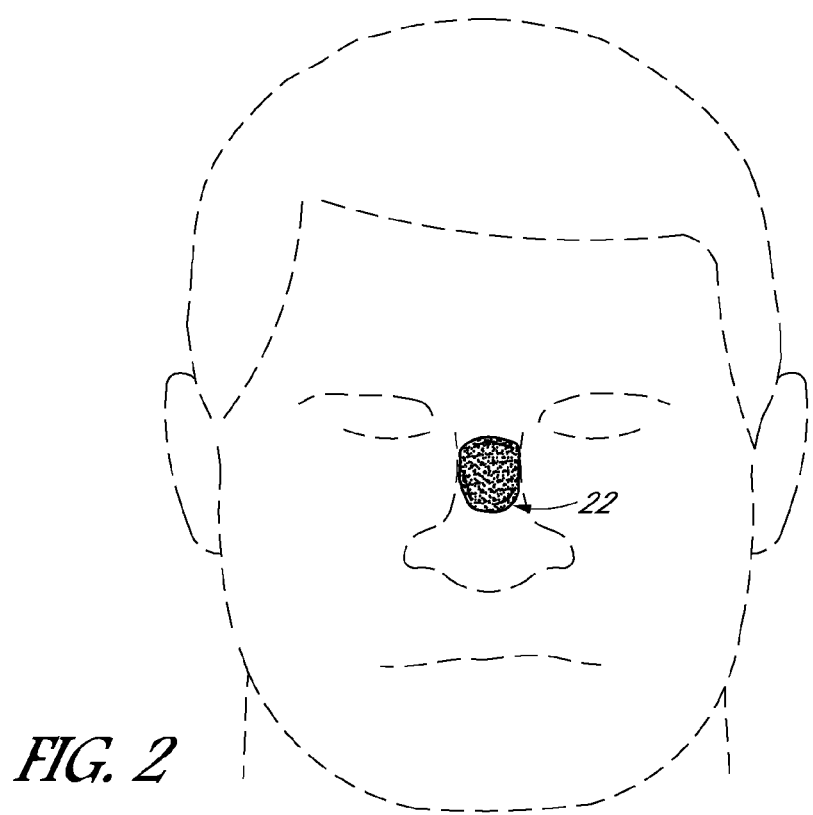
Figure 3:
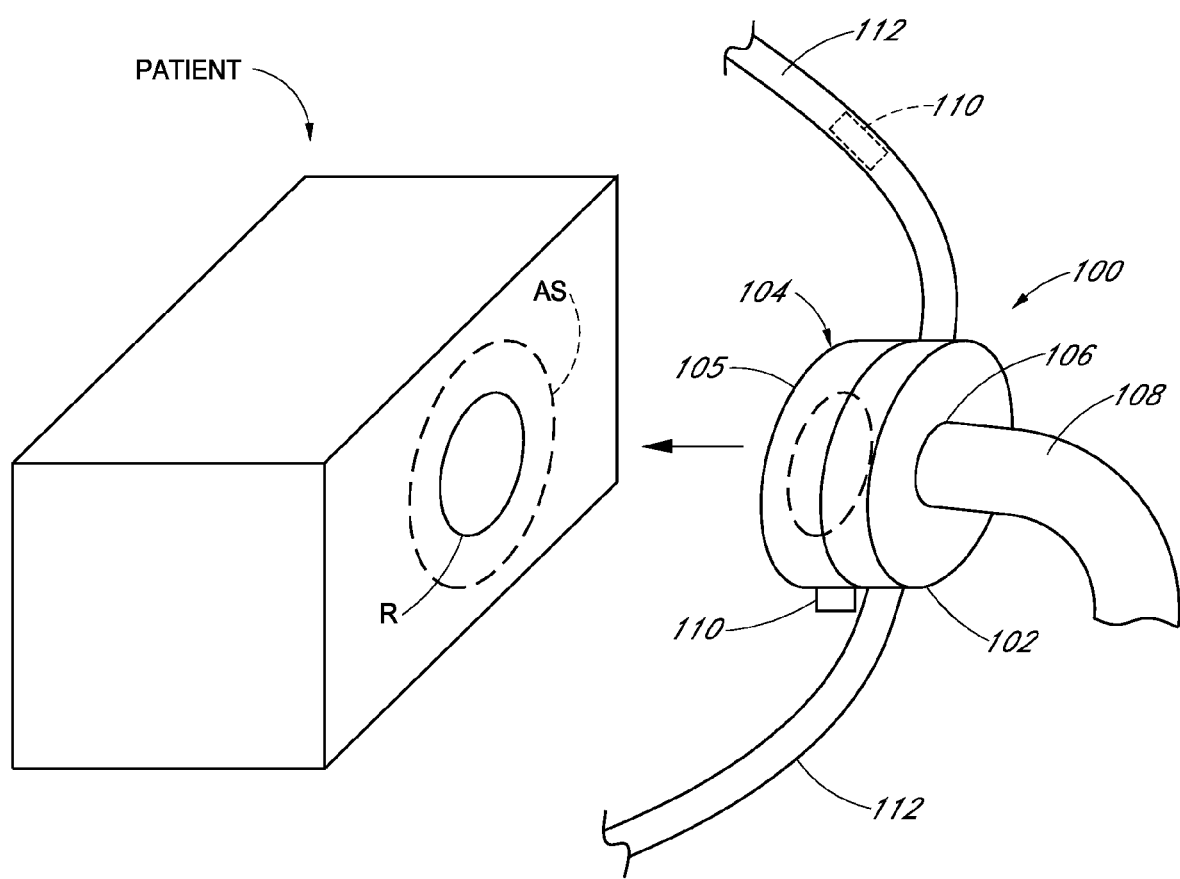
FIG. 3 is a schematic perspective and exploded view of a patient and a therapeutic fluid delivery device in accordance with an embodiment.

FIG. 3 schematically illustrates an embodiment of a therapeutic fluid delivery device 100 including at least one force sensor 110 configured to detect a force imparted onto a patient at the seal-skin interface. As used herein, the term "force" is intended to encompass either a load or a pressure.

The fluid delivery device 100 can include a frame 102, a seal portion 104 and a conduit connection 106. The frame 102 can be configured to extend over a target portion R of a patient to be treated with the fluid delivery device 100. For example, but without limitation, the target area R can be an area of the patient's body, such as the patient's skin with an undesirable characteristic, such as disease, an incision, a wound or at least one respiratory orifice of a patient, which can be, for example but without limitation, the nostrils, nose, and/or mouth of a patient.

The conduit connection 106 can be in the form of a connection for receiving or discharging fluids or solids including those intended for therapies. For example, the conduit connection 106 can be in the form of a respiratory conduit connection, which can optionally be incorporated into an aperture of the frame 102 to provide connection to a respiratory air conduit. The fluid delivery conduit 108 can be of the type for supplying any type of fluids or solids intended for therapeutic uses, such as a flow of pressurized breathable gases to the fluid delivery device 100. Optionally, the fluid delivery device 100 can include a strap assembly 112 for securement to a patient.

The fluid delivery device 100, as noted above, can be configured for providing a sealing arrangement with respect to a target portion R of the patient's body, such as the skin, or one or any combination of a patient's respiratory orifices, such as one or both nostrils (e.g., nasal masks), the mouth (oral masks), tracheotomy incisions, as well as other types of wounds, incisions, orifices, or areas to be treated with the fluid delivery device 100. As such, the seal portion 104 can include a sealing surface 105 configured to generate a seal with an area or portion of the patient AS surrounding any one or any combination of the target portions R noted above. The portion AS can be in the form of skin, hair, with or without or other structures intended to be left in place during use of the fluid delivery device, such as a mask 100, such as a nasogastric tube. Additionally, in any of the above noted configurations, the fluid delivery device 100 can also include one or any combination of the various features disclosed herein, including various types of sensor, sensor configurations, sensor orientations, and other concepts described in greater detail below.

The sensor 110 can be any type of force sensor and can be mounted to the seal portion 104 or the frame 102. The force sensor 110 can be configured to detect a force imparted onto an area AS by the seal portion 104. For example, the force sensor 110 can be configured to detect a force imparted to the sealing surface 105 by way of contact with the area AS.

Optionally, the fluid delivery device 100 can include a plurality of sensors 110 disposed in different locations. For example, the plurality of sensors 110 can be positioned at different locations on the frame 102 and/or the seal portion 104. The sensor 110 can be configured to detect a force imparted onto the fluid delivery device 100, such as forces imparted onto the sealing surface 105, by way of contact with the area AS, and to output a signal indicative of the detected force. Further, optionally, the fluid delivery device 100 can include one or more sensors associated with the strap assembly 112, illustrated as sensor 110 in phantom line, for detecting forces associated with holding the fluid delivery device 100 against the patient.

The sensor 110 can also be connected to driver electronics (not shown) configured to convert the signal from the sensor 110 to a value indicative of the detected force. Optionally, and described in greater detail below, the driver electronics can be connected to a display device for displaying a representation of the detected force in any format.

Figure 4:
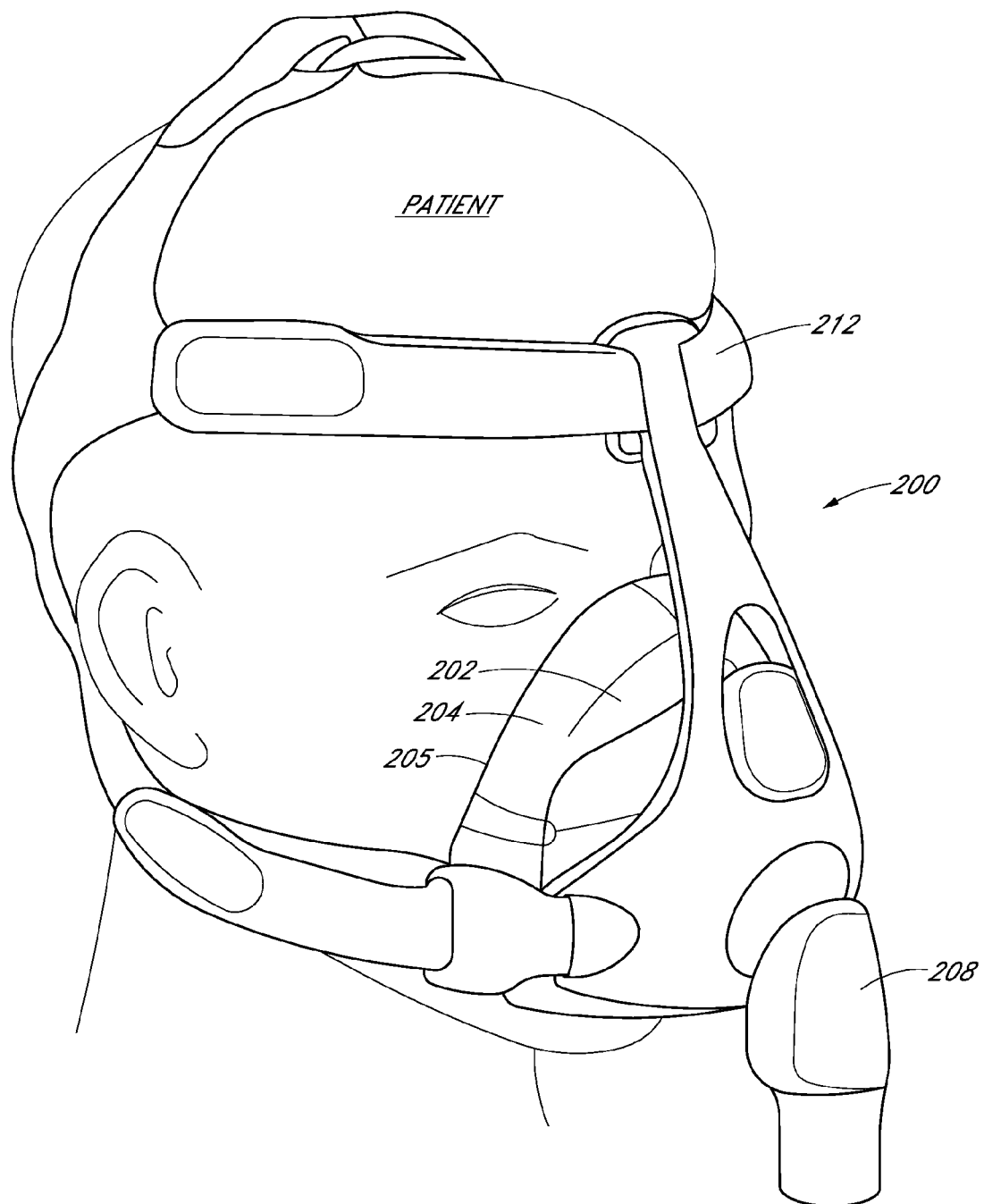
FIG. 4 is a perspective view of an embodiment of the device of FIG. 3, in the form of a respiratory mark fitted on a patient and including a head strap assembly.

FIG. 4 illustrates an embodiment of the fluid delivery device 100 of FIG. 3, in the form of a respiratory mask, identified generally by the reference numeral 200. Parts, features and components of the mask 200 that correspond to the same or similar parts, features and components of the fluid delivery device 100 are identified with the same reference numeral except that a fluid delivery device 100 has been added thereto.

In the embodiment of FIG. 4, the mask 200 includes a frame portion 202 and seal portion 204 that are configured to extend over both the mouth and the nose of a patient. Thus, the target area R of the mask 200 is the nose and mouth of the patient.

The sealing surface 205 can be configured to form a seal with the area of skin AS (FIG. 3) which extends over the bridge of the patient's nose and around the mouth in a generally teardrop shaped configuration, as is well known in the art. The respiratory conduit 208 can deliver a therapeutic fluid, such as breathable gasses, to the patient by passing through the conduit connector 206, into the frame portion 202 and into the space between the patient's face, the frame portion 202 and the surrounding seal portion 204. Additionally, the mask 200 can include a strap arrangement 212 configured for retaining the mask 200 against a patient's face.

Figure 5:
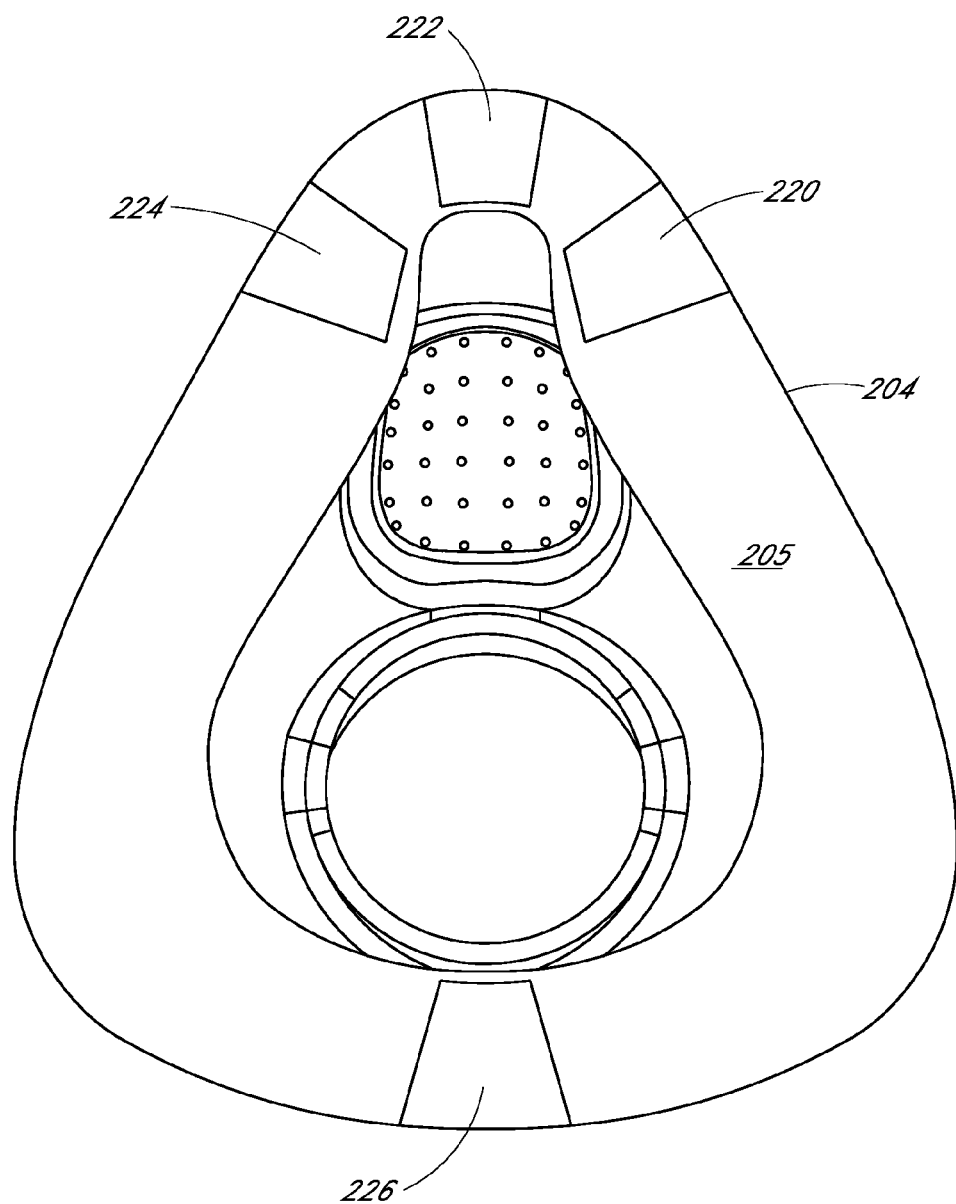
FIG. 5 is a rear elevational view of the mask of FIG. 4 with the straps removed.

With reference to FIG. 5, in some embodiments, the seal portion 204 of the mask 200 can include a plurality of sensors 220, 222, and 224 proximate to the nose bridge portion of the mask 200. As viewed in FIG. 5, the sensor 220 would be proximate to the right side of the bridge of the patient's nose, sensor 224 would be on the left side of the bridge of the patient's nose, and the sensor 222 would be positioned proximate to the top of the bridge of the patient's nose. Additionally, optionally, the mask 200 can include a sensor 226 disposed at a lower portion of the seal portion 204 proximate to a patient's chin during use. Each of the sensors 220, 222, 224, 226 can be configured to detect a force imparted to the patient's skin by the portion of the sealing surface 205 at the respective locations or proximate to the respective locations of the sensors 220, 222, 224, 226.

In some embodiments, the mask 200 includes at least two of the sensors 220, 222, 224, 226. By incorporating at least two sensors into the mask 200, differences in the forces applied to the patient's skin can be detected and used to assist fitment of the mask 200 onto a patient. Thus, in some embodiments, the mask 200 includes a plurality of sensors, for example, sensors 220, 222, and 224 proximate to the nose bridge portion of the mask. As such, force differences around the bridge of a patient's nose can be detected and used for assisting fitment of the mask 200 on a patient.

In some embodiments, the mask 200 includes at least one sensor 226 proximate to the chin portion of the mask 200 and at least one additional sensor, for example, at least one of the sensors 220, 222, 224.

Figure 6A:
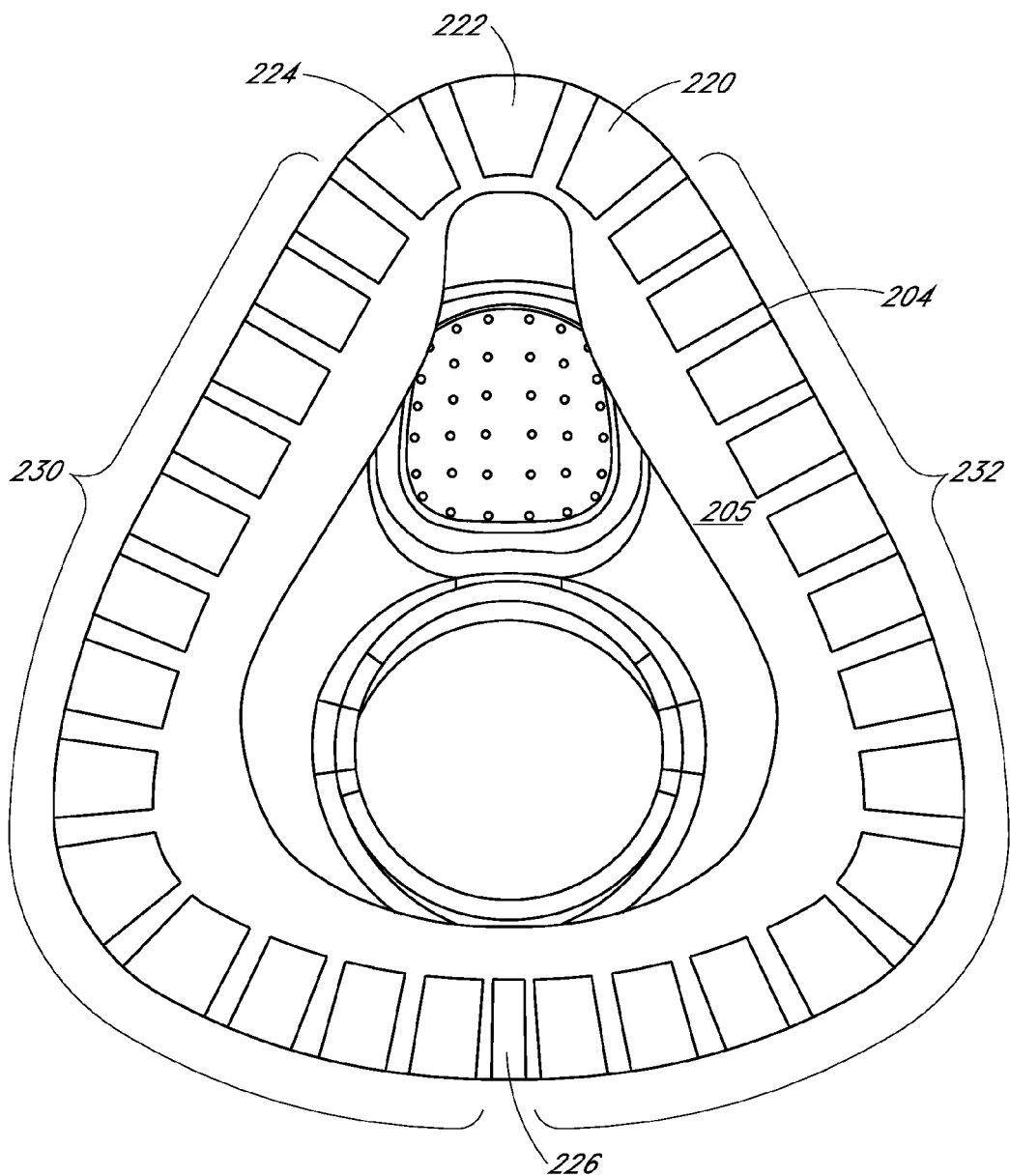
FIG. 6a is a rear elevational view of a modification of the mask illustrated in FIG. 5.

FIG. 6a illustrates an optional arrangement of sensors on the seal portion 204. In the optional arrangement of FIG. 6a, the seal portion 204 includes the plurality of sensors 220, 222, 224 proximate to the nose bridge portion of the mask 200, sensor 226 proximate to the chin portion of the mask 200, as well as additional sensors, identified as left side plurality of sensors 230 and right side plurality of sensors 232 which, when combined with sensors 220, 222, 224, and 226, form an approximately evenly spaced array of sensors extending around the entire periphery of the seal portion 204. Spacing variations between the sensors on the order or 1-3 millimeters would be considered as encompassed by the term "approximately evenly" spaced, although other ranges of spacings, at greater distances, can also be used and considered as "approximately evenly" spaced. In such an arrangement, the sensors can detect and generate signals indicative of forces at a greater number of locations around the periphery of the seal portion 204. Thus, such sensor outputs can be used to provide data sufficient for, for example, a higher resolution mapping of the forces imparted onto the patient's skin by the seal portion 204.

Figure 6B:
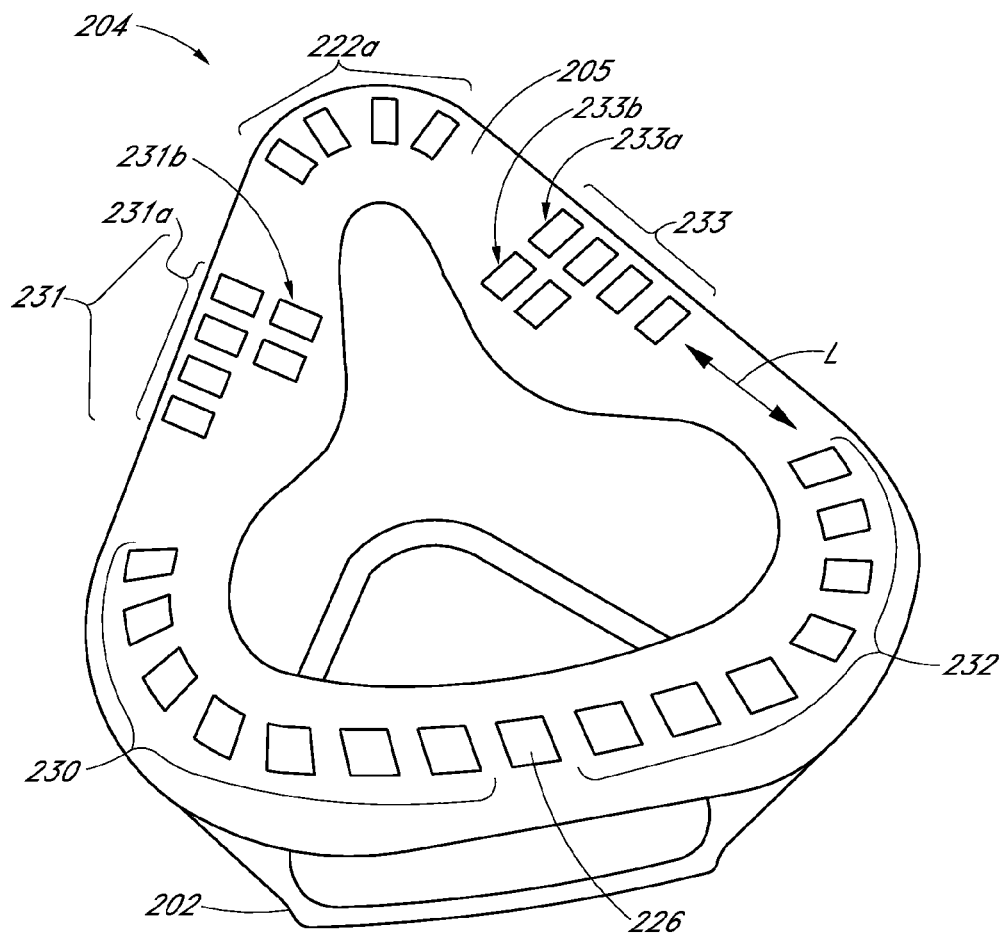

FIG. 6b illustrates a modification of the seal portion 204 including a different arrangement of sensors. In the embodiment of FIG. 6b, the seal portion 204 includes a plurality of sensors 222a proximate to the nose bridge portion, left side plurality of sensors 230, right side plurality of sensors 232, and sensor 226 positioned to be proximate to a chin of a patient. Additionally, the seal portion 204 also includes a left side cluster of sensors 231 and a right side cluster of sensors 233, which are positioned along the sealing surface 205 so as to be proximate to the left and right sides of a patient's nose. Additionally, as illustrated in FIG. 6b, the left and right clusters 231, 233 include a plurality of rows of sensors extending along the length L direction of the sealing surface 205.

For example, as shown in FIG. 6b, the left side cluster includes an outer row 231a and an inner row 231b. Similarly, the right side cluster includes an outer row 233a and an inner row 233b. Including the plurality of rows of sensors can help improve the detection and understanding of the sealing effect occurring at locations including multiple rows of sensors.

For example, in the embodiment of FIG. 6b, the rows 231a, 231b, 233a, 233b are positioned so as to lie approximately at the transition between the sides of the user's nose and the adjacent upper cheek portions of the user's face. Such use of additional sensors and/or a higher density of sensors can provide a benefit of higher resolution force information. Additionally, such use of multiple rows of sensors can help a user determine where along the sealing surface 205 a seal may be generated, for example, more towards an inner side of the seal portion 204 or more towards an outer side of the seal portion 204. In some embodiments, such enhanced force detection ability can help identify and thus resolve leaks near a patient's eye. For example, the areas of the seal portion 204 in the vicinity of clusters 231, 233 can result in leaks which direct air or jets of air toward a user's eyelashes or eye which can result in discomfort for the patient. Thus, such additional sensors can be used to help identify and resolve leaks which may be caused, for example, by insufficient skin pressure.

FIG. 6c illustrates an optional embodiment of the strap arrangement 212, identified generally by the reference numeral 212a. The strap assembly 212a includes an upper strap assembly 240, a lower strap assembly 242 and a cradle member 244. The cradle member 244 is designed to rest against the back of a patient's head. The upper strap assembly 240 is configured to connect an upper portion of the mask 200 to a corresponding upper portion of the cradle member 244 and the lower strap assembly 242 is configured to connect a lower portion of the mask 200 with a lower portion of the cradle member 244. The upper and lower strap assemblies 240, 242 can include any number of clips, straps, tensioning devices, etc., as is known in the art. Additionally, the upper and lower strap assemblies 240, 242 and/or the cradle member 244 can include one or more sensors configured to detect a force.

For example, the mask 200 can include any arrangement of anchor points for connection to the strap assembly 212*a*. In the illustrated embodiment, the mask 200 includes an upper anchor head 246, a lower left anchor point 248, and a right side lower anchor point (not shown).

The upper anchor head 246 includes left and right apertures 247, 249 for engagement with tension adjustment assemblies 250. For example, the upper strap assembly 240 can include a left side tension adjustment assembly 250 and a right side tension adjustment assembly 251.

The left and right tension adjustment assemblies 250, 251 include an engagement end configured to engage with the apertures 247, 249, respectively. Additionally, the left and right tension adjustment assemblies 250, 251 include distal ends 252, 253, respectively configured for engagement with adjustable portions of the upper strap assembly 240. For example, in the illustrated embodiment, the upper strap assembly 240 includes adjustable strap portion 254 on the left end and adjustable strap portion 255 on the right end. In the illustrated embodiment, the adjustable strap portion 254, 255 can be in the form of any type of strap including an adjustable fixation device, for example, but without limitation, hook and loop fasteners. The lower strap assembly 242 can include the same or similar arrangement of tension adjustment assemblies and adjustable straps.

Optionally, the upper strap assembly 240 can include one or more force sensors. For example, the upper strap assembly 240 can include a force sensor 256 incorporated into the tension adjustment assembly 250. In some embodiments, the upper strap assembly 240 can include a sensor assembly 257 including a force sensor disposed on a different portion of the upper strap assembly 240, for example, spaced from the adjustable strap portion 254. Similarly, the lower strap assembly 242 can include a force sensor 256*a* incorporated into the tension adjustment assembly 250*a* and optionally a force sensor 257*a* incorporated into the lower strap assembly 242, as well as sensors at other locations, such as location 257*a*.

With continued reference to FIG. 6*c*, the head strap assembly 212*a* can optionally include a head sensor 260 configured to detect a force between the cradle member 244 and a back of a patient's head. For example, the sensor 260 can be configured to detect a normal or compressive force at the location schematically illustrated in FIG. 6*c*. Additionally, optionally, the strap arrangement (e.g., the head strap assembly) 212 can include an optional neck force sensor 262. For example, the sensor 262 can be disposed at a lower portion of the cradle member 244 and can be configured to detect a force between the cradle member 244 and a neck of a user. For example, the sensor 262 can be configured to detect a compression between the cradle member 244 and the neck of a user.

With continued reference to FIG. 6*c*, the mask 200 can include an optional conduit tension sensor 264 configured to detect a tension in the conduit 208. For example, a portion of the conduit 208 can be formed with the sensor 264 such that the sensor 264 is loaded in tension when the conduit 208 is subjected to a tensile force in the direction of arrow T of FIG. 6*c*.

Each of the sensors of the head strap assembly 212*a* noted above can be configured as separate sensor assemblies, each including its own sensor driver, power supply, and communication device. Alternatively, all the sensors of the head strap assembly 212*a* noted above can be divided into groups, each group connected to a common sensor driver, power supply, and/or communication device. Further, optionally, all the sensors noted above can be connected to a single sensor driver, power supply, and communication device. The outputs of such sensors can be used, processed, or converted, for purposes of determining forces, values indicative of forces, or values having a proportional or other predictable and/or predetermined mathematical relationship to forces imparted to a patient's head by way of the strap assembly 212*a* and mask 200. Similarly, the output from the sensor 264 can be used to determine forces associated with tension in the conduit 208. Such information on the force imparted onto the conduit 208 can also be used to determine how forces on the conduit 208 affect forces in the strap arrangement 212 and the mask 200.

With continued reference to FIG. 6*c*, the mask 200 can include any of the optional sensor configurations described above. Alternatively, in some embodiments, the mask 200 includes a sensor assembly 210 which is configured and positioned to detect forces acting between the frame portion 202 and the seal portion 204 of the mask 200. Such a configuration of a sensor is described in greater detail below with reference to FIGS. 14*b*, 15*a*, and 15*b*.

FIG. 6*d* illustrates a modification of the mask 200 including a modified lower left anchor point 248*a*. In the illustrated embodiment, the lower left anchor point 248*a* includes an optional integrated force sensor 265. The optional force sensor 265 can be configured to detect a tensile force applied to the lower left anchor point 248*a*. For example, the sensor 265 can be positioned and configured to detect a tensile force (or other forces) imparted onto the lower left anchor point 248*a*, for example, by way of a lower strap assembly 242 (FIG. 6*c*). Optionally, a lower right anchor point 248*b* can also include an optional force sensor 265.

FIGS. 6*e*-6*j* illustrate various different optional configurations for sensors that can be integrated or applied to a head strap assembly of a mask, for example, the head strap assembly 212*a* (FIG. 6*c*). Each of the variations is identified generally by the reference number 257, generally corresponding to a sensor assembly corresponding to the sensor assembly 257, and with a letter added corresponding to the associated figure numbers of FIGS. 6*e*-6*j*, respectively.

With reference to FIG. 6*e*, the sensor assembly 257*e* can be in the form of a detachable sensor unit configured to be releasably engagable with a portion of the strap assembly 212*a*, such as the upper or lower strap assemblies 240, 242. For example, the upper head strap assembly 240 illustrated in FIG. 6*c* can include an outer covering configured to provide releasable engagement with a fastener, for example, a hook and loop type fastener. Other types of outer coverings and fasteners can also be used.

Thus for example, the upper strap assembly 240 can include an outer fabric like covering including a loop type structure consistent with a hook and loop type fastener engagement. The sensor assembly 257*e* can include a corresponding outer covering, for example, a hook type structure configured to provide a releasable engagement with the outer loop type covering of the upper strap assembly 240. Additionally, the sensor assembly 257*e* can include a sensor 268 configured to detect a tension in the sensor assembly 257*e*. For example, the sensor 268 can be configured to detect tension in the direction of arrow T of FIG. 6*e*. Thus, when the upper strap assembly 240 is stretched, the hook and loop fastener attaching the sensor assembly 257*e* to the upper strap assembly 240 is also subjected to a tension, thereby imparting a tension onto the sensor 268. Thus, the sensor 268 can be configured to detect a force associated with such imparted tension and to output a signal indicative of such force.

In the configuration of FIG. 6f, the sensor assembly 257f can have essentially the same construction as the sensor assembly 257e and can be used to connect two free ends of the upper strap assembly 240.

With reference to FIG. 6g the sensor assembly 257g can include a sensor 268 disposed within a hollow portion of the associated upper strap assembly 240. For example, opposite longitudinal ends of the body of the sensor 268 can be fixed to spaced apart portions of the upper strap assembly 240, for example, with stitching, glue, pins, or any other structure.

FIGS. 6h-6j illustrate further optional configurations for the incorporation of sensors into strap assemblies. For example, FIG. 6h illustrates an optional configuration in which a sensor assembly 257h is integrated with the upper strap assembly 240 so as to be exposed on the outer surfaces of the upper strap assembly 240. Optionally, as shown in FIG. 6i, the sensor assembly 257 can be disposed within the upper strap assembly 240 so as to be flush with an outer surface of the upper strap assembly 240, identified as the sensor assembly 257ie. Alternatively, as shown in FIG. 6i, the sensor assembly 257ii can be integrated with the upper strap assembly 240 so as to be flush with the inner surface of the upper strap assembly 240, and covered on the outer side of the upper strap assembly 240, with an outer layer thereof.

Further, optionally, FIG. 6j illustrates a configuration in which the sensor assembly 257j is laminated between the inner and outer layers of the upper strap assembly 240. Other configurations can also be used.

Figure 6K:
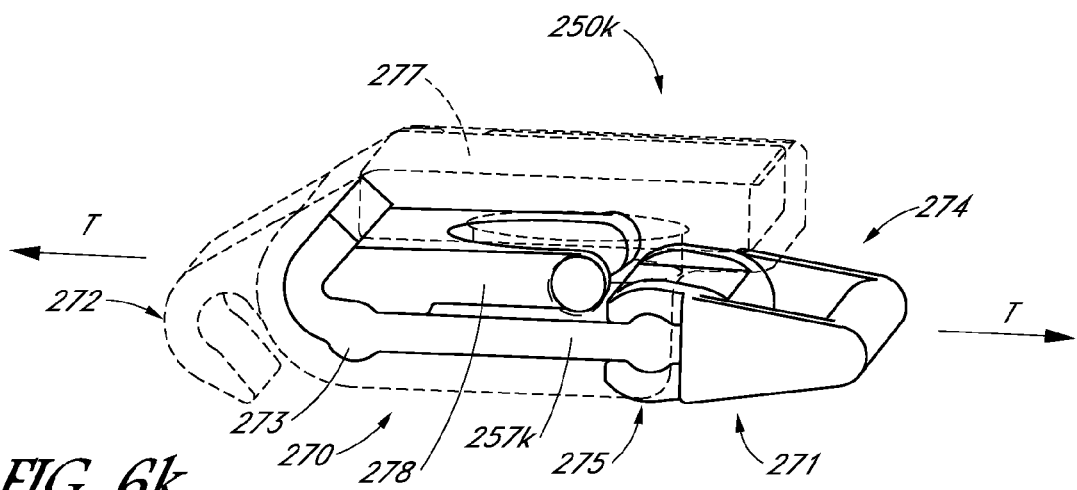
FIG. 6k is a perspective, partial wire frame view of a head strap clip that can be used with the mask of FIG. 6c and including a sensor.
Figure 6L:
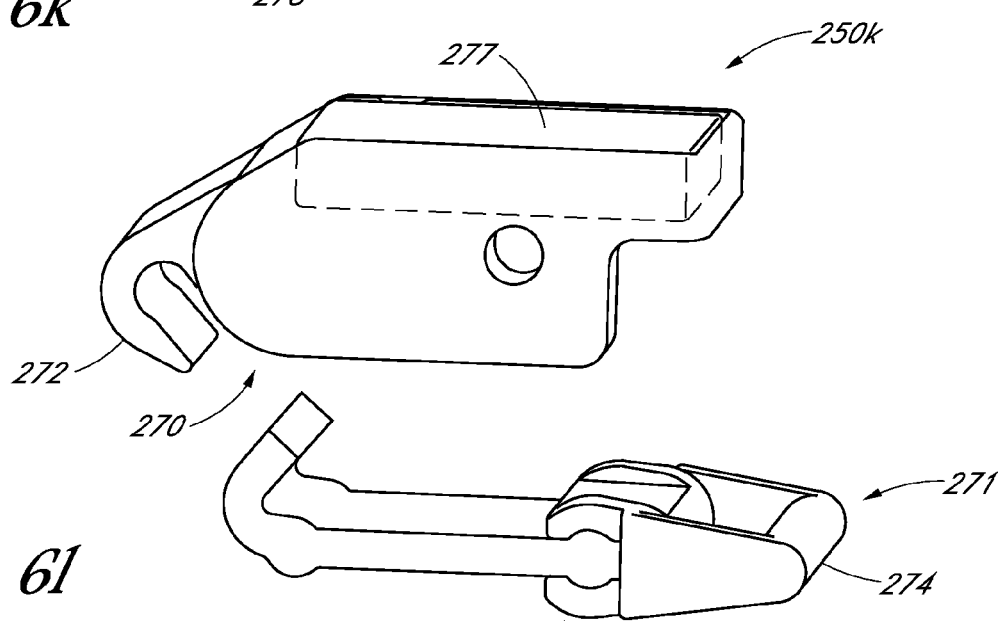
FIG. 6l is a perspective exploded view of the clip of FIG. 6k.
Figure 6M:
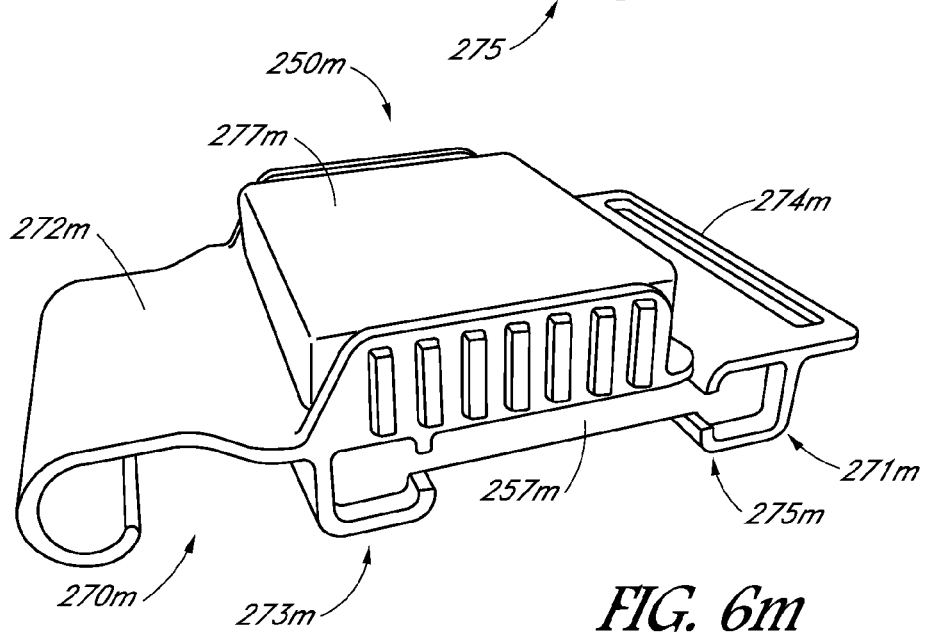
FIG. 6m is a perspective view of a modification of the clip of FIG. 6k.

FIGS. 6k, 6l, and 6m illustrate optional configurations of clips that can be used with the strap assembly 212a, for example, in place of the tension adjustment assemblies 250a, 251, 250a. FIGS. 6k and 6l illustrate one optional configuration, identified generally by the reference numeral 250k.

As shown in FIGS. 6k and 6l, the tension adjustment assembly 250k can include a first portion 270, a second portion 271 and a sensor body 257k connecting the first and second portions 270, 271. The first portion 270 can include an engagement portion 272 configured to engage a portion of the mask 200. For example, the engagement portion 272 can be in the form of a hook shaped member configured to fit into an aperture, such as the aperture 247 (FIG. 6c). The first portion can also include a sensor retaining clip 273 configured to fix an end of the sensor body 257k to the first portion 270.

The second portion 271 of the tension adjustment assembly 250k can include a further engagement device 274 configured to engage, for example, a strap of the strap assembly 212a, such as the upper strap assembly 240 and the adjustable strap portion 254 (FIG. 6c). For example, the engagement device 274 can include an aperture configured to receive the adjustable strap portion 254. Other configurations can also be used. Further, the second portion 271 can include a sensor body engagement portion 275 configured to fix an end of the sensor body 257k to the second portion 271. As such, when the tension adjustment assembly 250k is subjected to a tensile force, for example, in the direction of arrow T, the sensor body 257k is subjected to a tension force. The sensor[[y]] body 257k can be configured to output a signal indicative of the tension force applied thereto.

Figure 16:
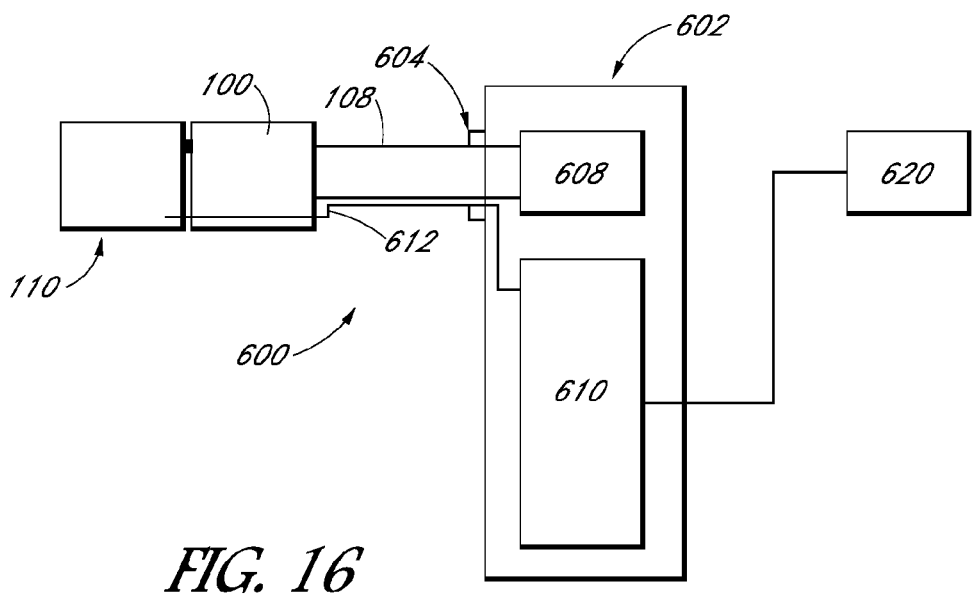
FIG. 16 is a schematic diagram of a fitment system including any of the fluid delivery device embodiments disclosed above and a display device.
Figure 17:
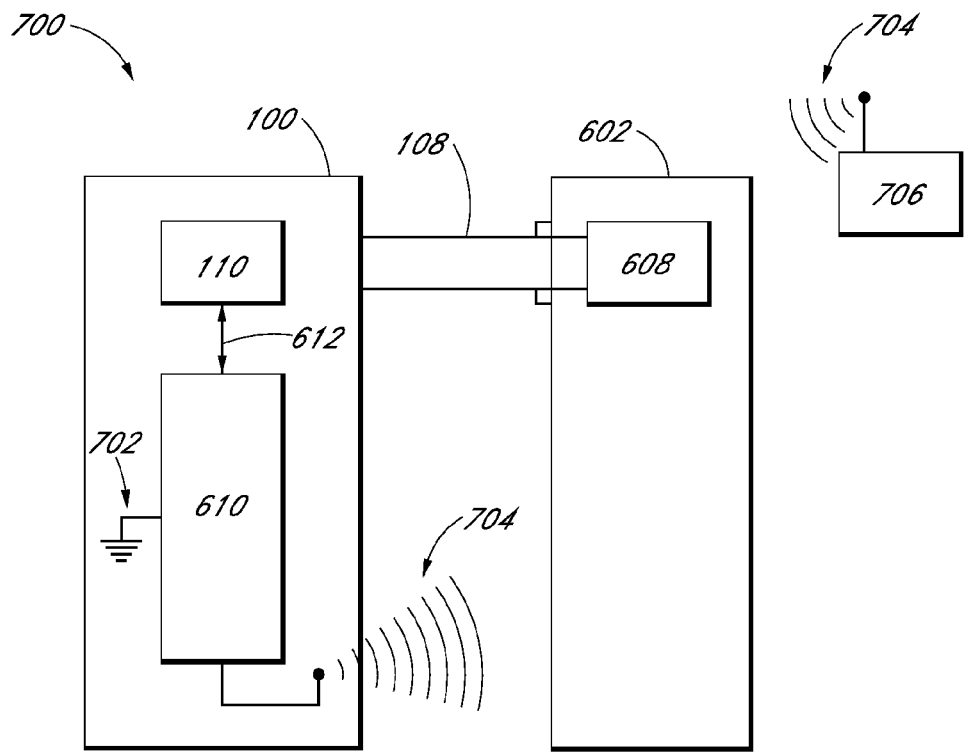
FIG. 17 is a schematic diagram illustrating a wireless embodiment of the fitment system of FIG. 16, including a wireless display device.

Optionally, the tension adjustment assembly 250k can include a driver module portion 277 including, for example, but without limitation, a sensor driver for the sensor body 257k, a power supply, and/or a communication device. The driver module portion 277 can be constructed, optionally, in accordance with the description set forth below with reference to sensor driver 610 (FIGS. 16 and 17).

Optionally, the tension adjustment assembly 250k can include a pressing boss 278 shaped and configured to maintain alignment and engagement of the sensor body 257k in the first portion 270. As illustrated in FIG. 6k, one end of the sensor body 257k fixed to the first portion 270 can be bent upwardly toward the driver module portion 277. As such, conductors, leads, wires, etc., connected with the electrodes of the sensor body 257k can be connected with the electronics within the driver module portion 277.

FIG. 6m illustrates a modification of the tension adjustment assembly 250k, identified generally by the reference numeral 250m. Features, parts, and components of the tension adjustment assembly 250m that are similar or the same as corresponding parts, components, and features of the tension adjustment assembly 250k are identified with the same reference numeral, except that a letter "m" has been added thereto.

With the continued reference to FIG. 6m, the tension adjustment assembly 250m includes a first portion 270 connected with a first end of the sensor body 257m and a second portion 271m fixed to a second opposite end of the sensor body 257m. In the embodiment of FIG. 6m, the tension adjustment assembly 250m engages the sensor body 257m with the sensor body 257m in a flat configuration, the first portion of the tension adjustment assembly 250m engaging a terminal end of the sensor body 257m with the first engagement portion 273m. The opposite end of the sensor body 257m is fixed to the second portion 271m with the second engagement portion 275m. Conductors (not shown) connecting the electrodes of the sensor body 257m with the electronics within the driver module portion 277m can extend from the first end of the sensor body 257m, upwardly through the first portion 270m, into the sensor driver assembly 277m. Other configurations and electrical connections can also be used.

Figure 7:
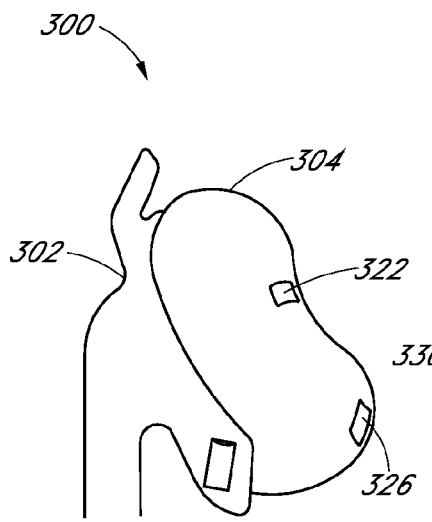
FIG. 7 is a perspective view of another embodiment of the mask, in the configuration of an oral mask.
Figure 8:
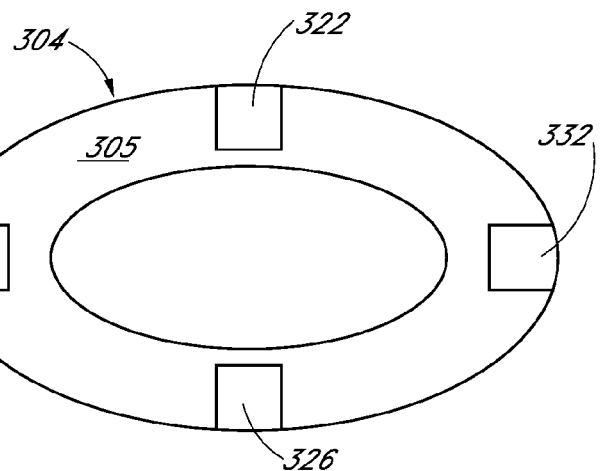
FIG. 8 is a rear elevational view of the mask of FIG. 7.

FIGS. 7 and 8 schematically illustrate a further modification of the masks 100 and 200, and as identified generally by the reference numeral 300. Parts, features, and components of the mask 300 that are similar or the same as the masks 200 are identified with the same reference numeral except that a 100 has been added thereto.

The mask 300 can be configured to extend only around the mouth of a patient. Thus, the target area R (FIG. 3) for the mask 300 corresponds to the patient's mouth. The mask 300 includes a frame 302 and a seal portion 304.

With reference to FIG. 8, the seal portion can include one or a plurality of sensors. For example, the seal portion can include a sensor 322 disposed at the center of the top portion of the seal portion 304, configured and positioned to be proximate to the center of the area of skin between a patient's nose and upper lip and optionally sensor 326 configured and positioned to lie proximate to the chin of the user. Optionally, the seal portion can include a left side sensor 330 and a right side sensor 332.

In further optional embodiments, the seal portion 304 can include an additional plurality of sensors (not shown) spaced and arranged relative to the sensors 322, 326, 330, 332 to form a generally evenly spaced array of sensors around the entire periphery of the seal portion 304.

Figure 9:
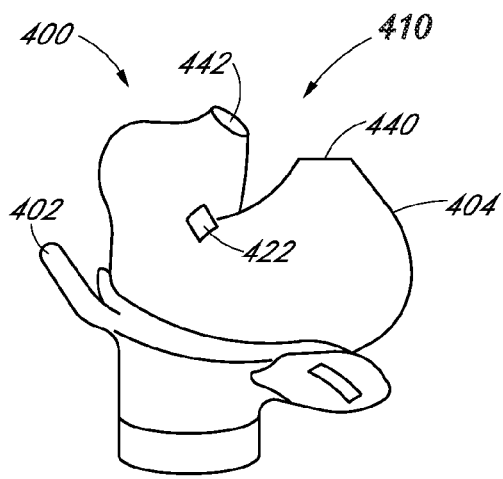
FIG. 9 is a perspective view of another modification of the mask in the configuration of a nasal pillow mask.

FIG. 9 illustrates yet another modification of the mask 100, identified generally by the reference numeral 400. Parts, features, and components of the mask 400 that are the same or similar to the mask 300 are identified with the same reference numeral except that a 100 has been added thereto.

The mask 400 is configured to function as a nasal pillow mask. As such, the mask 400 includes a frame portion 402 mounted to a pillow type nasal seal portion 404.

The seal portion 404 includes two upwardly extending fluid ports, including a left side fluid port 440 and a right side fluid port 442. The fluid ports 440, 442 extend from the body of the seal portion 404 upwardly and tapering toward their upper, distal ends. During use, these fluid ports 440, 442 would extend into the nostrils of a patient.

Figure 10:
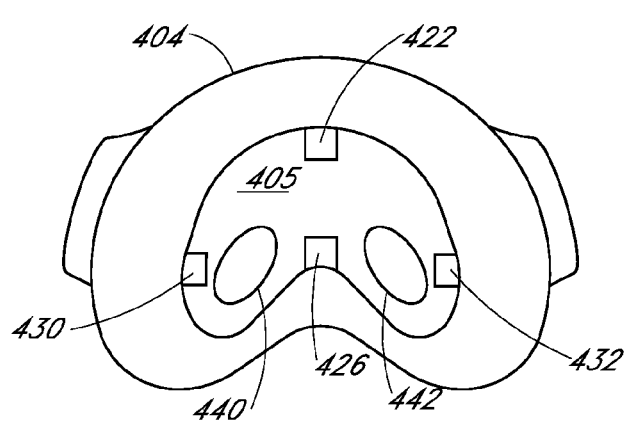
FIG. 10 is a skewed view of the nasal mask, as viewed along the direction identified by the arrow 410 in FIG. 9.

FIG. 10 is a skewed top view of the mask 400 as viewed along the arrow 410. of FIG. 9. As shown in FIG. 10, the sealing surface 405 extends around both of the fluid ports 440, 442 in the area shaped and configured to contact and seal against the skin surrounding the nares of a patient.

In some embodiments, the seal portion 404 can include one or a plurality of sensors. For example, the mask 400 can include a sensor 422 positioned and configured to lie proximate to the bottom surface of a distal portion a patient's nose. Optionally, the seal portion 404 can include a sensor 426 positioned and configured to lie proximate to the portion of a patient's nares proximate to the uppermost portion of the patient's upper lip. Additionally, the mask 400 can include a left side sensor 430 configured to lie proximate to a left side of a patient's left nostril. Additionally, the mask 400 can include a right side sensor 432 configured and positioned to lie proximate to the right side of a patient's right nostril. Further, optionally, the mask 400 can include an additional plurality of sensors (not shown), optionally combined with the sensors 422, 426, 430, 432 to form a generally evenly spaced array extending around the entire sealing surface 405.

The sensors described above with regard to the fluid delivery devices (i.e., masks) 100, 200, 300, and 400, can be any type of force sensor, including load sensors and pressure sensors. In some embodiments, the sensors described above can be in the form of dielectric elastomer stretch sensors, which are commercially available and capable of measuring a range of forces, including compressive, tension, shear, and bending forces. Dielectric elastomer stretch sensors can operate as flexible or soft capacitors. The sensors can also be known as electro-polymer sensors or elastic capacitive sensors which can also be configured to measure tension. It is possible to adapt these sensors to measure other forces, including but not limited to compression, bending, shear or a combination of forces. Additionally, sensors can be used in other locations than those identified above. For example, sensors can be positioned so as to detect force applied to any delicate area of the skin or delicate area of the face, such as philtrum, septum, nasal bridge, chin, or any part of the body made of cartilage or any portion of the face where the skin is proximate bone.

With reference to FIG. 11, the sensor 500, which can be used as any of the sensors described above or below, is in the form of an elastic capacitive sensor. The sensor 500 can be made from a laminated elastomer structure which enables it to be flexible, stretchable and compressible. The sensor 500 can include a first outer surface 502 and a second outer surface 504 and a dielectric layer 506 comprising an intervening compressible material. For example, the first and second outer surfaces 502, 504 can be in the form of conductive silicone. The dielectric layer 506 can be in the form of nonconductive silicone, or in other words, silicone that serves as an insulator and can also be referred to as a dielectric layer 506. Optionally, the entire sensor 500 can be encapsulated in additional outer layers (not shown) of nonconductive silicone, or other nonconductive material, so as to encapsulate the sensor 500.

Constructed as such, the outer surfaces 502, 504, made from a conductive material, such as conductive silicone, carbon black, or other conductive materials, form the electrodes of a capacitor, spaced apart and electrically isolated from each other by the dielectric layer 506. As such the capacitance of the thus formed capacitor changes along with changes in the shape and/or spacing of the outer surfaces 502, 504.

For example, as shown in FIG. 12, when the outer surfaces 502, 504 are pressed toward each other so as to reduce the spacing x therebetween, causing the surface area of the outer surface 502 to increase and thus increase the capacitance of the sensor 500. Additionally, when the sensor 500 is subjected to a tensile force (arrow T), for example, horizontally oriented in FIG. 11, the outer surfaces 502, 504 are elongated, thereby increasing the surface area of the electrodes formed by the outer surfaces 502, 504, and thus increasing the capacitance of the sensor 500. The sensor 500 can be manipulated and/or distorted in other ways that also affect the capacitance of the sensor 50. These changes in capacitance can be detected by an appropriate driver, as well known in the art, and can be optionally converted into a values indicative of or in a predictable or predetermined mathematical relationship with forces imparted to the sensors. As such, the sensor 500 detects deformation of itself and/or, depending on the configuration of the connection of the sensor 500 to a portion of a mask, the sensor 500 detects deformation of the mask by way of the deformation of the sensor 500 caused by deformation of the mask.

Elastic capacitive sensors can have several benefits in the context of the use of respiratory masks. For example, elastic capacitive sensors can be curved and bent in their neutral position without changing the output signal of the sensor. This allows the sensors to conform to three dimensional curvatures of a mask or a patient's face but not change an output signal until an external force is applied. This essentially limits bias in the sensors. Measurements provided by capacitive sensors can be stable and can be less significantly influenced by bending in the same manner or to the same degree as resistive sensors. This is a result of the distance between the laminated layers of the outer surfaces 502, 504 remaining substantially constant when bent. Other sensor types, such as resistive sensors, can be prone to drift, noise and temperature or environmental deviations, which make them less accurate and reliable than elastic capacitive sensors in certain environments of use.

With reference to FIG. 12a, when not attached to another surface, an electro capacitive sensor 500 has a neutral axis 510 which passes through the center of the sensor mass. When bent, one surface of the sensor, outer sensor 504, will expand while the other 502 will retract; thus cancelling out the difference of capacitive change caused by the changes of the outer surfaces 504, 502.

Thus, during manufacturing, such a sensor 500 can be bent (e.g., FIG. 12a) to follow the contours of the desired mounting location of the sensor 500 on a seal portion 204 when the seal portion 204 is in an unloaded, neutral state. Then the sensor can be affixed (FIG. 12b) to the seal portion 204 in the desired manner with the sensor 500 also remaining in a neutral state in that its capacitance is the same or nearly the same as when it is unbent.

With continued reference to FIG. 12b, after the sensor 500 is affixed to another surface (e.g., an inner surface of the seal portion 204), however, the neutral axis 510 is translated to the plane adjoining the sensor 500 and surface portion 204. When the sensor 500 is subsequently bent, the fixed surface 504 cannot expand/retract freely, while a measurable change in surface area will still occur on the opposite free side of the outer surface 502. This change in surface area can be measured and correlated to a change in bend force. As such, the sensor 500 can be optionally configured to detect a bending force applied to the seal portion 204. For example, the sensor 500 can be secured to an inner surface of the seal portion 204, at least partially extending onto the area of the side wall of the seal portion 204 adjacent to the sealing surface 205. In some embodiments, the sensor 500 is mounted so that it is positioned on a side wall of the seal portion 204 and spaced from the sealing surface 205. As such, the output of the sensor can be considered as an indication of only bending of the seal portion 204 (when sensor 500 is spaced from the sealing surface 205) or as a combination of bending of the seal portion 204 and compression at the sealing surface 205 (when it extends onto both the sidewall and over the sealing surface 205).

With reference to FIGS. 12c-12i, force sensors, such as any of the force sensors described above, can be formed in different configurations, which can provide additional benefits.

Figure 12C:
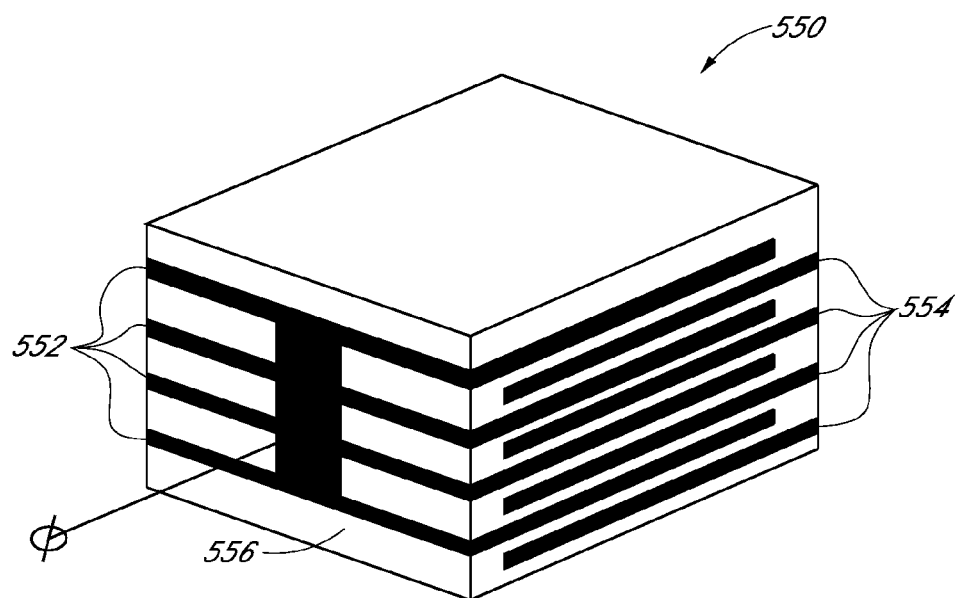
FIG. 12c is a schematic perspective view of a modification of the sensor of FIG. 11 in a layered configuration and including interleaved electrodes.
Figure 12D:
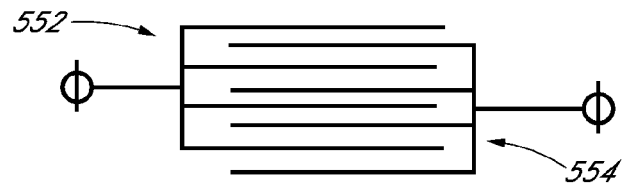
FIG. 12d is a schematic view of the sensor of FIG. 12c illustrating electrical connections of interleaved electrodes.

For example, FIGS. 12c and 12d illustrate a modification of the sensor 500, identified generally by the reference numeral 550. Parts, components, and features of the sensor 550 that are the same or similar to corresponding parts, components, or features of the sensor 500 are identified with the same reference numeral except that "50" has been added thereto.

With continued reference to FIG. 12c, the sensor 550 can include a plurality of layers that are essentially made up of the sensors 500. For example, the sensor 550 can include electrodes 552, 554 arranged in an interleaved manner with dielectric material 556 disposed between each of the electrodes 554, 552 and on the outer surface of the sensor 550. In such an arrangement, the sensor 550 is essentially a multi-layered, single capacitor, the capacitance of which changes with deformation, for example, compression, bending, elongation, etc. Such a multi-layered configuration of the sensor 550 can provide higher resolution sensing.

In such a configuration, the sensor 550 includes multiple layers of capacitors laid on top of each other in a configuration in which they share electrodes which reduces the total thickness of the sensor 550. This can be beneficial because stacking sensors provides output resolution as a function of thickness; thus it becomes possible to keep the thickness of the sensor 550 minimal on areas of a mask which do not require high resolution, thereby minimizing surface disturbances of the mask in the vicinity of the sensor 500 and using thicker layered sensors on areas in which higher resolution can be beneficial. Such layered sensors 550 can further dramatically increase the total capacitance of the sensor 550, which not only increases the resolution and range of output values, but also increases the signal to noise ratio which can lead to more reliable, consistent, and/or precise output values.

Figure 12E:
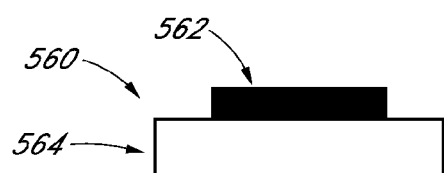
FIG. 12e is a schematic side elevational view of another optional sensor component configuration.

With reference to FIG. 12e, a layered sensor, such as the sensor 550, can be formed through the combination or layering of a plurality of preformed layered capacitor components, such as component 560 shown on FIG. 12e, which includes a conductive layer 562 and a dielectric layer 564.

Figure 12F:
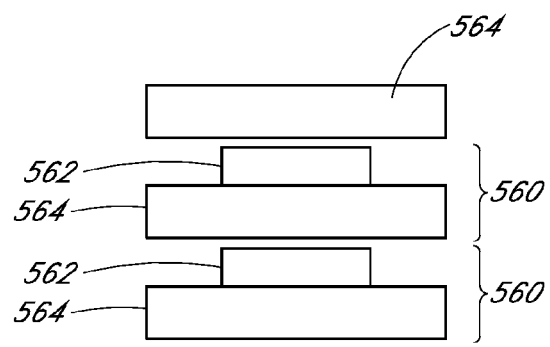
FIG. 12f is a schematic side elevational view of a combination of plural sensor components of FIG. 12e.

With reference to FIG. 12f, individual pieces of the component 560 can be layered one on top another so as to form the basic capacitor configuration of two electrodes 562, spaced by a dielectric layer 564. Adding an additional dielectric layer, for example, on top as viewed in FIG. 12f can be added for encapsulation, as desired. Such a method of construction of a sensor can provide additional benefits.

Figure 12G:
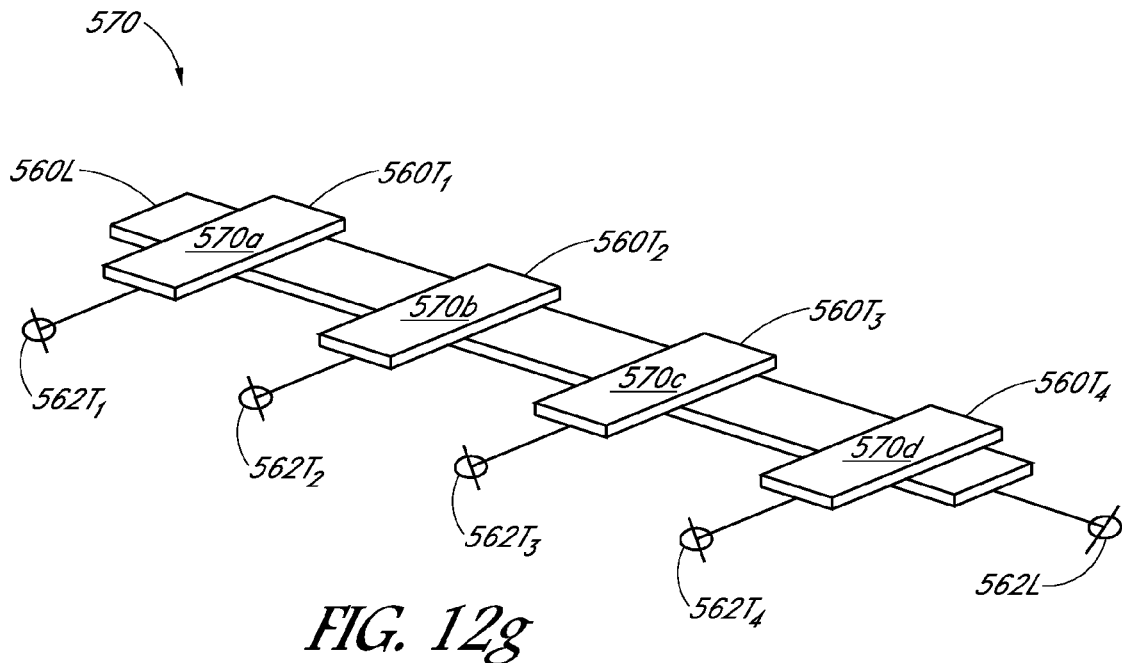
FIG. 12g is a schematic perspective view of a sensor arrangement formed of one sensor component overlapped by four transverse sensor components.
Figure 12H:
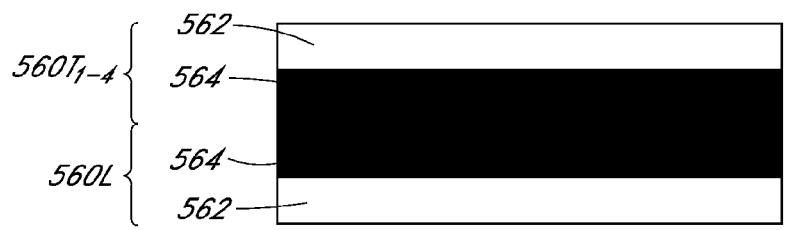
FIG. 12h is a schematic side elevational view illustrating overlapping portions of the sensor arrangement of FIG. 12g.
Figure 12I:
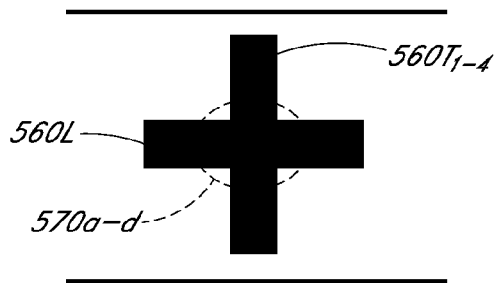
FIG. 12i is a top plan view of the overlapping arrangement of FIG. 12h.

For example, with reference to FIG. 12g, a transversely layered sensor 570 can be formed with a plurality of units 560. For example, more specifically, the sensor 570 can include a longitudinal unit 560L and a plurality of transverse units $560T_1$, $560T_2$, $560T_3$, $560T_4$. As described above with reference to FIGS. 12e and 12f, the units 560L, $560T_{1-4}$ can be arranged so as to create pairs of electrodes 562 spaced by dielectric layers 564. For example, with reference to FIGS. 12i and 12h, in the vicinity of locations in the sensor arrangement 570 of FIG. 12g, where the layers 560L and $560T_{1-4}$ overlap, pairs of electrodes spaced by dielectric layers can be formed. For example, with reference to FIG. 12h, in the vicinity of the overlapping areas illustrated in FIGS. 12g and 12i, the unit 560L includes a lower electrode 562 and an upper dielectric layer 564. As such, the electrode 562 of the unit 560L provides a common electrode for each of the individual capacitors formed in the unit 570. For clarity, each of the overlapping areas of the sensor 570 illustrated in FIG. 12g are identified as 570a, 570b, 570c, 570d.

The upper electrode 562 of each of the sensors 570a-d is formed by the electrodes associated with the units $560T_{1-4}$. In such a configuration, the electrode 562L (FIG. 12g) of the unit 560L can be connected to a driver (not shown) and serve as the electrode for all of the sensors 570a-d. However, the electrodes $562T_1$-$T_4$, while they can be connected to a single sensor driver, would normally be read in a serial fashion because using a common electrode 562L for each of the sensors 570a-570d would require a serial sampling scheme.

Depending on the mounting location, loading dynamics, and sensor configuration, including any of the above-described sensors 500, 550, 570, etc., the output of the sensor 500 can be tested against known loads on the sealing surface 205 to establish a predetermined relationship between the output of the sensor 500 and loads applied to the sealing surface 205. In the description set forth below, force sensors are referred to by the reference numeral 500, although it is intended that any of the descriptions including reference to a sensor 500, applies to all of the sensor configurations described above.

For example, the output signal of the sensor 500 can be fit with a polynomial curve (e.g., $2^{nd}$ order, $3^{rd}$ order, $4^{th}$ order, $5^{th}$ order, $6^{th}$ order, etc.) for defining a proportional relationship between capacitance values indicated by the output of the sensor 500 and the force imparted to the sealing surface 205.

Any of the sensors described above can be integrated with various different types of seal portions of masks. For example, FIG. 13a is a schematic cross-section of a portion of the mask 200 in which the mask 200 is formed of a stiffer frame portion 202, which can be made from polycarbonate or other more rigid or more flexible materials and with a silicone sealing portion 204 over-molded onto a portion of the frame portion 202. For example, more particularly, the frame portion 202 illustrated in FIG. 13a can include a conduit connector 206 disposed on a distal portion of the mask 200, and a proximal portion 207, positioned to lie more proximal to a user's face during use. The seal portion 204 can include a distal portion 203 that is over-molded onto the proximal portion 207 of the frame portion 202. The seal portion 204 can include varying geometry, for example, thicknesses, extending from the distal portion 203 to the inner edge 209. The sealing surface 205 would normally lie between the distal portion 203 and the inner edge 209.

In some embodiments, the mask 200 can include an arrangement of the sensors 500 disposed at the sealing surface 205. For example, FIG. 13b illustrates a sensor 500 mounted to the outer surface of the sealing surface 205. For example, the sensor 500 can be bonded to, co-molded or over-molded with the sealing surface 205.

Optionally, the sensor 500 can be partially or fully embedded into the seal portion 204. For example, FIG. 13c illustrates the sensor 500 being partially embedded in the seal portion 204 so as to be partially protruding from the sealing surface 205. FIG. 13d, on the other hand, illustrates an optional mounting configuration of the sensor 500 wherein the outer surface of the sensor 500 is flush with the sealing surface 205.

The mounting configuration of FIG. 13b can result in the sensor 500 being more responsive to forces applied thereto, for example, forces resulting in compression of the sensor 500. The arrangement of FIG. 13d, with the outer surface of the sensor 500 being flush with the sealing surface 205, can provide better sealing performance and leak reduction between the user and the sealing surface 205. The partially protruding configuration illustrated in FIG. 13c provides a mix of the benefits of enhanced sensitivity provided by the partially protruding arrangement and the enhanced sealing and/or leak reduction provided by partially embedding the sensor 500 into the seal portion 204.

Figure 14D:
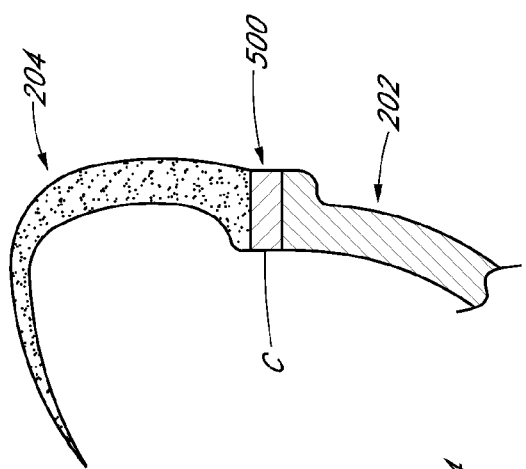
Figure 14B:
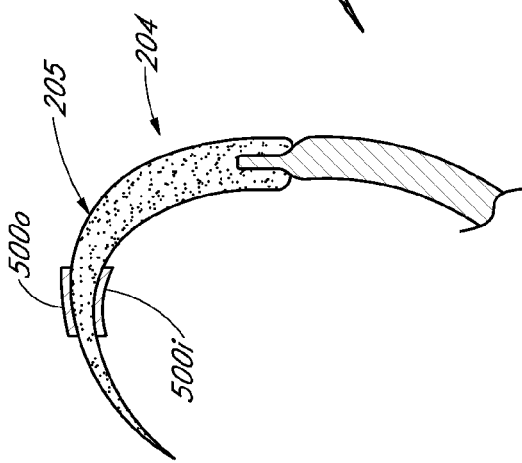
FIG. 14b is an enlarged sectional view of the mask of FIG. 14a illustrating a pair of sensors, one mounted on an external side with the sealing portion of the mask and one sensor mounted on an interior side.
Figure 14C:
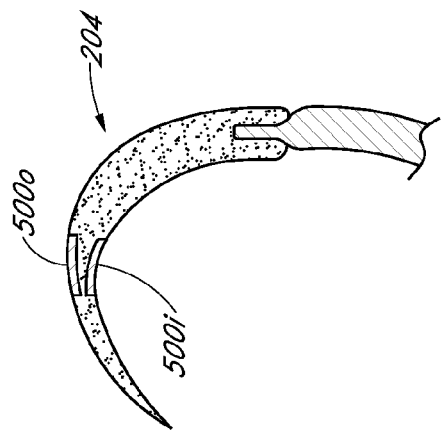
FIG. 14c is an enlarged sectional of the mask of FIG. 14a illustrating a modification of the arrangement of FIG. 14b including a partially or flush mounted exterior side sensor and a partially embedded or flush mounted interior side sensor.
Figure 14A:
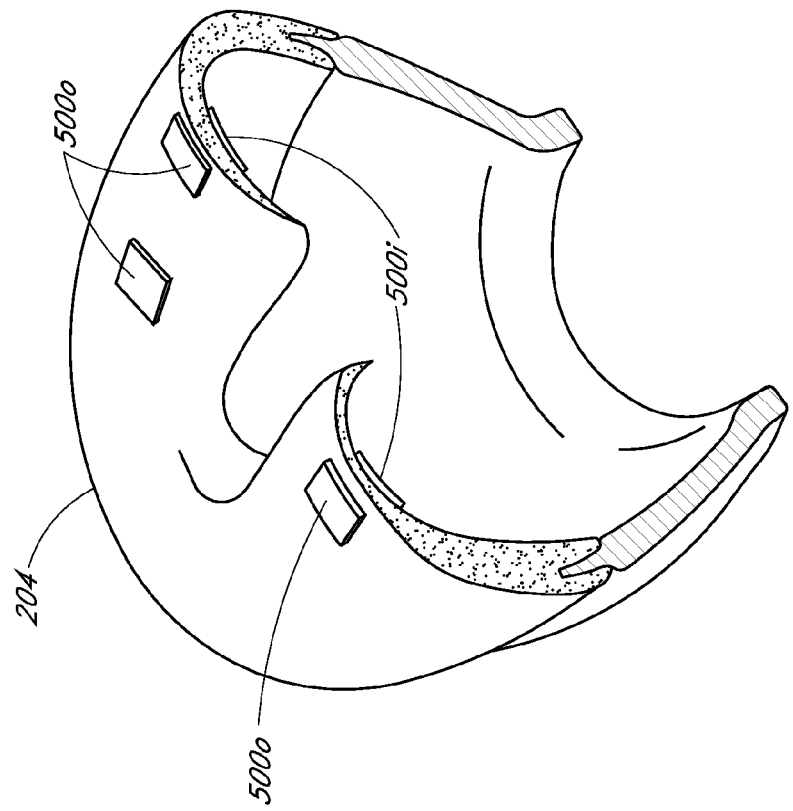
FIG. 14a is a schematic and perspective cross-sectional view of a portion of the mask of FIG. 4 illustrating a dual-sensor mounting arrangement.

With reference to FIGS. 14a-14c, the sensors 500 can optionally be arranged in a dual or "paired" sensor configuration. For example, with reference to FIG. 14a, pairs of sensors 500 can be mounted to the seal portion 204 wherein, for example, outer sensors 500o are paired with inner sensors 500i, aligned with one another, as illustrated in FIGS. 14a and b. In the embodiments of FIGS. 14a and b, the sensors 500o, 500i are mounted to the inner and outer exposed surfaces of the seal portion 204, for example, in the configuration of the mounting of sensor 500 to the sealing surface 205 illustrated in FIG. 13b. Optionally, with reference to FIG. 14c, the sensors 500i, 500o can be mounted as to be partially embedded (FIG. 13c) or flush mounted (FIG. 13d) with the surfaces of the seal portion 204. Optionally, the sensors 500o, 500i can be mounted in the same position and orientation on the seal portion 204. Configured as such, the mask 200 can be placed on a user's face and tightened so as to cause the seal portion to be compressed and to bend. As the seal portion 204 distorts, the sensors 500o, 500i can be deformed and generate a sensor output. The output of the sensors 500o, 500i will follow a relationship with the deformation of the sensors 500o, 500i, which can include bending and compression. Optionally, it may desirable to process the output from the sensors 500o, 500i so as to isolate compression. Thus, in some embodiments, the output from the sensors 500o, 500i can be overlaid so as to eliminate the deformation caused by bending. Thus, the resulting signal will more closely represent compression applied to the sealing surface 205.

Further, optionally, the sensor 500 can be disposed at the interface between the frame portion 202 and the seal portion 204. In such a configuration, the sensor 500 would be loaded more in compression than other loading.

Optionally, any of the sensors 500 described above can be mounted and/or connected to a seal support or a foamed or gel sealing portion. For example, FIG. 15a illustrates a variation of the mask 200 including a support portion 201 connected to the frame portion 202 and shaped and configured to provide structural support to the sealing portion 204. For example, the support portion 201 can be in the form of foamed or gel material. Additionally, the support portion 201 can extend around a limited portion or the entire inner periphery of the seal portion 204, so as to provide resilient support for the seal portion 204, to thereby resist collapse of the seal portion 204 during use.

In some embodiments, a sensor 500 can be mounted at a proximal portion of the support portion 201, for example, at a position generally between the proximal end of the support portion 201 and the inner surface of the seal portion 204. This mounting location is identified by the reference numeral 500A. Optionally, a sensor 500 can be disposed within the interior of the support portion 201, for example, at the position identified by the reference numeral 500B. Further, optionally, a sensor 500 can be mounted in between the support portion 201 and the frame portion 202, in the position identified by the reference numeral 500C. Optionally, the embodiment of FIG. 15a can include sensors 500 at any one or any combination of the locations identified as 500A, 500B, 500C.

Figure 15B:
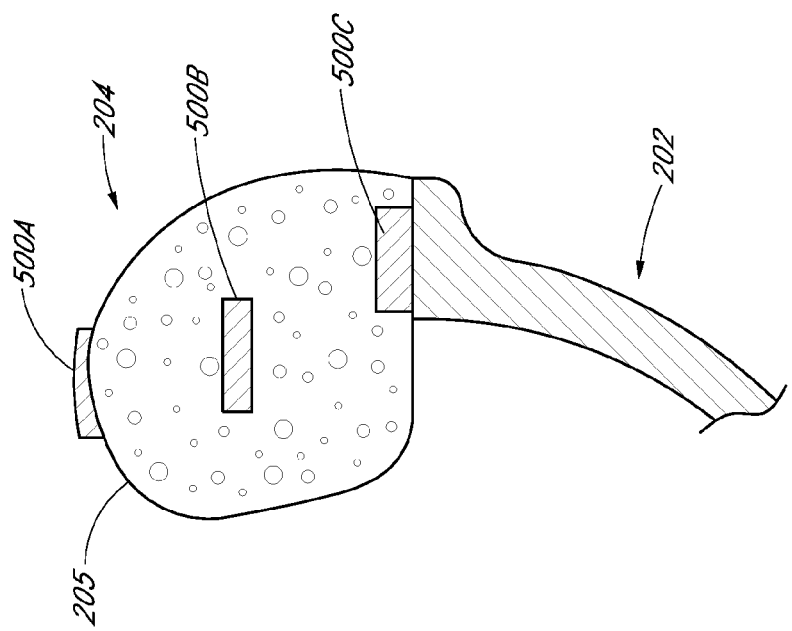
FIG. 15b is another enlarged schematic sectional view of an alternative sensor mounting location for a mask incorporating a cushion-type seal.
Figure 15A:
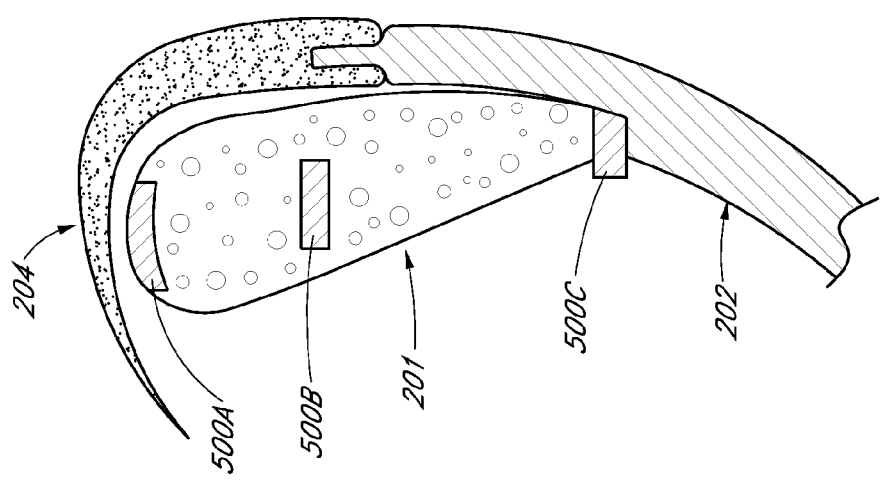
FIG. 15a is an enlarged schematic and sectional view of three optional sensor mounting locations for embodiments of the mask of FIG. 14a, including a cushion or gel portion.

FIG. 15b illustrates further modification of the mask 200, in which the seal portion 204 is formed of a foamed or gel material and is connected to the frame portion 202. Similarly to the embodiment of FIG. 15a, the seal portion 204 of FIG. 15b can include any one or a combination of sensors 500 disposed at various locations, for example, including a sensor 500 mounted at the sealing surface 205, in the position identified as 500A, disposed within the seal portion 204 in the position identified by the reference numeral 500B or at a position between the seal portion 204 and the frame portion 202, in the position identified as 500C.

As described above, in embodiments where the seal portion 204 are formed by a foamed or a gel material, the sensors 500 can be mounted to the exterior of the foamed or gel portion or suspended within the foam component at a range of depths within the foam or gel. In such embodiments, the support portion 201 or the seal portion 204 are made from a compressible foamed or gel material. The sensors 500 are loaded by displacement of an exterior wall of the seal portion 204 or the support portion 201 so as to exert forces on the sensors 500. In such embodiments, the sealing surface 205 can be smoother with less severe or no protrusions, thereby providing better sealing performance.

In some embodiments, the sensor 500 can have outer surfaces made from materials that are equal or nearly equal in hardness to the hardness of the materials used for the sealing surface 205. For example, in some embodiments of the mask 200, the sealing surface 205 can be made from silicone and the outer surfaces 502, 504 of the sensor 500 can be made from silicone having the same or approximately the same hardness (or softness). For example, the sensor 500, including the outer surfaces 502, 504, the dielectric layer 506, can be formed with materials, such as silicones, that have approximately the same or lower Shore hardness value and/or Young's modulus, than those of the sealing surface 205. As such, the presence of the sensor 500 is less likely to be perceivable to the patient.

Further, the sensor 500 and/or any other materials or layers attached to or encasing the sensor 500 can be made from materials or in structure that have the same mechanical behaviors (stiffness, compressibility, rigidity, elasticity) as the seal portion 204, sealing surface 205, cushion material of the tension adjustment assembly 250, etc. This can further reduce the likelihood that the presence of the sensor would be perceivable by a patient and can reduce or eliminate effects on the functionality or performance of the sensor 500.

Optionally, one or more of the sensors can be provided with shielding with non-conductive (dielectric) layer, for example included in the seal portion 204. For example, shielding with conductive (and earthed) electrode can help attenuate the effects of noise from sources such as light bulbs etc. Optionally, electrodes of the sensor 500 can be made with metalized (conductive) fabric. In some embodiments, the sensor lead (e.g., lead wires) 612 (FIG. 17) from the sensor 500, which can be in the form of copper wires or other types of conductors, extend past the silicone to a direct connection with the circuit board of sensor driver 610.

In some embodiments, the seal portion 204 can include an integrated anchoring point for the sensor 500. For example, the seal portion 204 can include an embedded bead or cord forming a thicker section that serves as an attachment point. Additionally, the seal portion 204 can include embedded elasticated fabric to increase the tear-strength. Optionally, embedded fabric can be included to act as over-stretch limiter.

Further, the seal portion 204 can include elasticated inlay (fabric) to modify the spring constant of the seal portion 204 and/or the sensor 500. This allows tuning the elongation at a given load.

With reference to FIG. 16, any of the fluid delivery devices described above can be incorporated into a fitment system which can optionally be integrated with a therapeutic fluid delivery supply. For example, with reference to FIG. 16, a mask fitment system 600 is illustrated as being integrated with a therapeutic fluid delivery supply 602. The mask fitment system 600 can include any of the fluid delivery devices described above, however, for brevity, device 100 is identified and represented schematically in FIG. 16.

The fluid delivery conduit 108 is connected to a therapeutic fluid delivery supply 602, which can be any type of therapeutic fluid delivery device, such as a C-pap machine, or any other kind of ventilation, respiration, gas, liquid or therapeutic solid delivery system. The fluid delivery conduit 108 is connected to the therapeutic fluid delivery supply 602 with a connector 604 which leads to a therapeutic fluid source 608.

The sensor 110 schematically represented in FIG. 16 represents one or a plurality of sensors in any of the arrangements and/or configurations described above. The sensor 110 can be connected to a sensor driver 610, which in the illustrated embodiment, is integrated into the therapeutic fluid delivery supply 602. The sensor 110 is connected to the driver 610 with a sensor lead 612. The sensor lead 612 is intended to represent one or a plurality of leads, one lead for each of the sensors 110.

The driver 610 can be any type of commercially available sensor driver. In some embodiments, where the sensors 110 are in the form of elastic capacitive sensors, the driver 610 can be in the form of a commercially available sensor module. In the illustrated embodiment, the driver 610 is configured for a wired connection to the sensors 110 through serial type data wire bundle.

The driver 610 can be configured to output a signal, in the form of data, which can include numerical values indicative of the capacitance of the connected sensors 110, in a predetermined relationship to forces or pressures imparted onto the sensors 110. The output of the driver 610 can be processed, with predetermined mathematical relationships, such as optionally polynomial fits noted above, into data indicative of a pressure or force detected by the sensors 110 or values that have a predictable or predetermined mathematical relationship with the forces detected by the sensors 110. Optionally, such data output from the driver 610 can be fed to a display device 620 configured to display representation of the forces detected by the sensors 110.

For example, optionally, the display device 620 can be configured to display a graphical representation of the mask 100 and force values presented with the graphical representation of the mask, with the force value representations spatially correlated to the locations of the sensors 110 on the mask 100. Such optional display formats are described in greater detail below with reference to FIGS. 20 and 21.

FIG. 17 illustrates a modification of the mask fitment system 600, identified generally by the reference numeral 700. The fitment system 700 transmits sensor data wirelessly, as described below.

As shown in FIG. 17, in the fitment system 700, the sensor driver 610 is mounted on the mask 100, along with a power supply 702. The sensor driver 610 receives a signal from the sensor 110 through the sensor lead 612. In this embodiment, the sensor driver 610 is configured to wirelessly transmit a signal 704 indicative of the capacitance of the sensor 110. Optionally, the driver 610 can be in the form of a commercially available sensor driver with wireless connectivity.

The fitment system 700 can include a display device 706 configured to receive the wireless signal 704 and display a representation of the forces detected by the sensor 110. Optionally, the display device 706 can be in the form of a handheld computing device, such as any of a large number of smart phones which are currently widely commercially available, operating on an Android™ and iOS platforms. However, other types of wireless enabled display devices can also be used.

Figure 18:
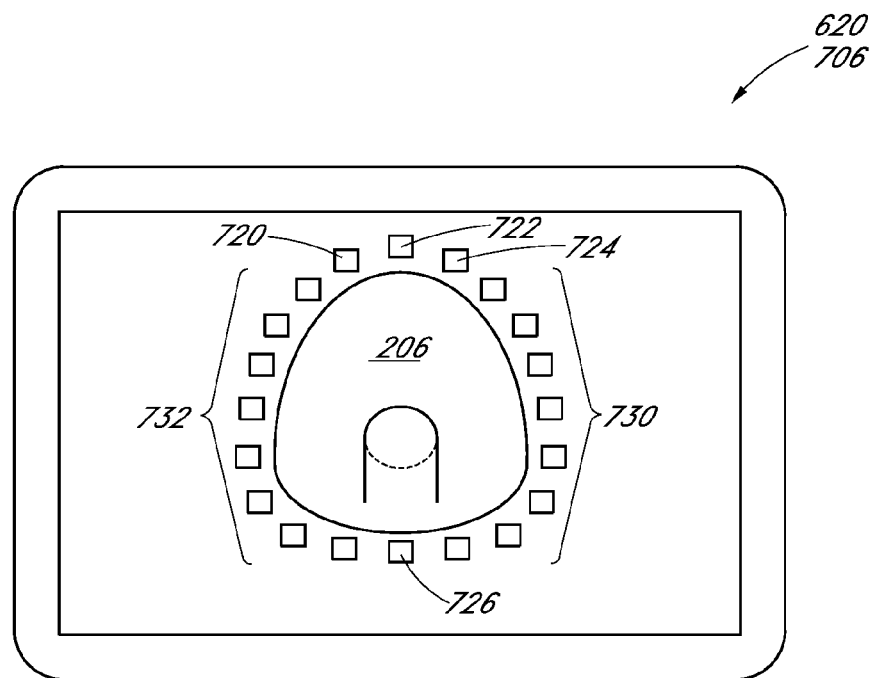
FIG. 18 is a schematic illustration of a display for displaying information indicative of forces detected by the force sensors, in a front elevational view orientation.

With reference to FIG. 18, the display devices 620 or 706 can be configured to display representations of the detected forces in various different formats. For example, as shown in FIG. 18, the display device 706 can be configured to display a graphical representation of the mask 200, corresponding to a front elevational view of the mask 200. Additionally, the display device 706 can be configured to display representations of the detected forces at locations spatially or positionally correlated or corresponding to the locations of the sensors 220, 222, 224, 226, 230, 232.

For example, the display device 706 can be configured to output a representation of the force detected by the sensor 220 (FIG. 6a) at representation 720. Similarly, the display device 706 can be configured to output representations from the sensors 222, 224, 226 at positions corresponding to representations 722, 724, and 726, respectively. Similarly, the display device can be configured to display representations of the plurality of sensors 230, 232 at the positions of representations 730, 732, respectively.

The representations 720, 722, 724, 726, 730, 732 can be in any format including numerical, iconic, color coded, or any desired format. Additionally, the position of the representations 720, 722, 724, 726, 730, 732 can be disposed on top of the graphical representation of the mask 200, or in any other desired location.

With the representations arranged in positions that generally correspond to the locations of the sensors, a user can more readily understand how to adjust a mask 200 based on the representations of the detected forces. In the display of FIG. 18, the graphical representation of the mask 200 is in a front elevational view orientation. Thus, a healthcare worker attempting to put the mask 200 onto a patient would see the representations of the forces in a way that corresponds to that person's view of the mask 200 which would also be in a front elevational orientation.

Using the representations of the forces as shown in FIG. 18, a healthcare provider could observe the representations of the forces, then adjust the mask 200 to achieve the most uniform force distribution around the periphery of the mask 200 as possible with the lowest magnitude of forces and with an acceptable leak rate.

Figure 19A:
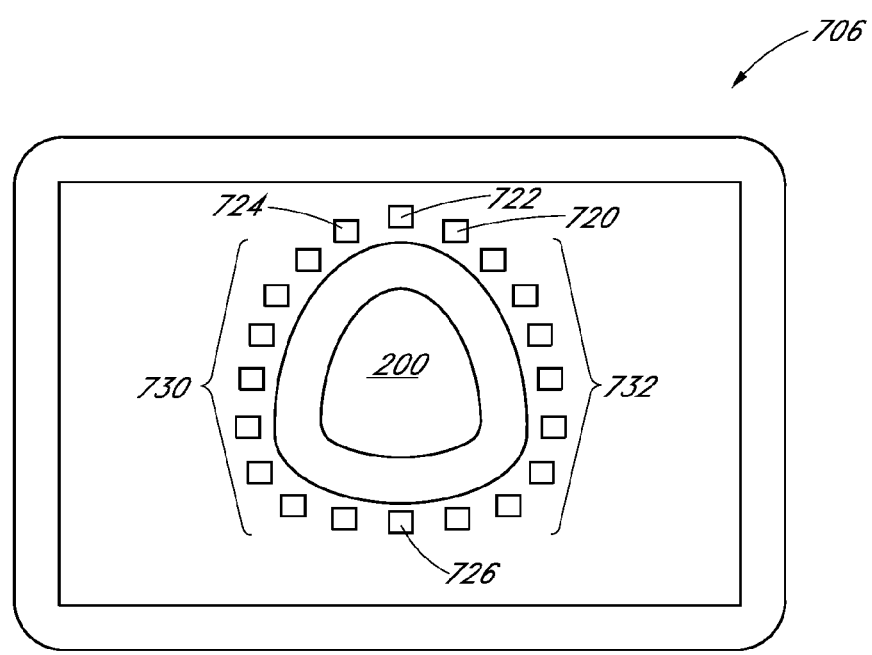
FIG. 19a is a schematic illustration of a graphical representation of force in a rear elevational view orientation.

With reference to FIG. 19a, optionally, the display device 706 can be configured to display a representation of the mask 200 in a rear elevational view. In this orientation, the representations 720 and 732 are disposed on the right side of the screen and the representations 724 and 730 are disposed on the left side of the screen. This orientation would be helpful to a patient attempting to fit the mask 200 on their own face.

Figure 19B:
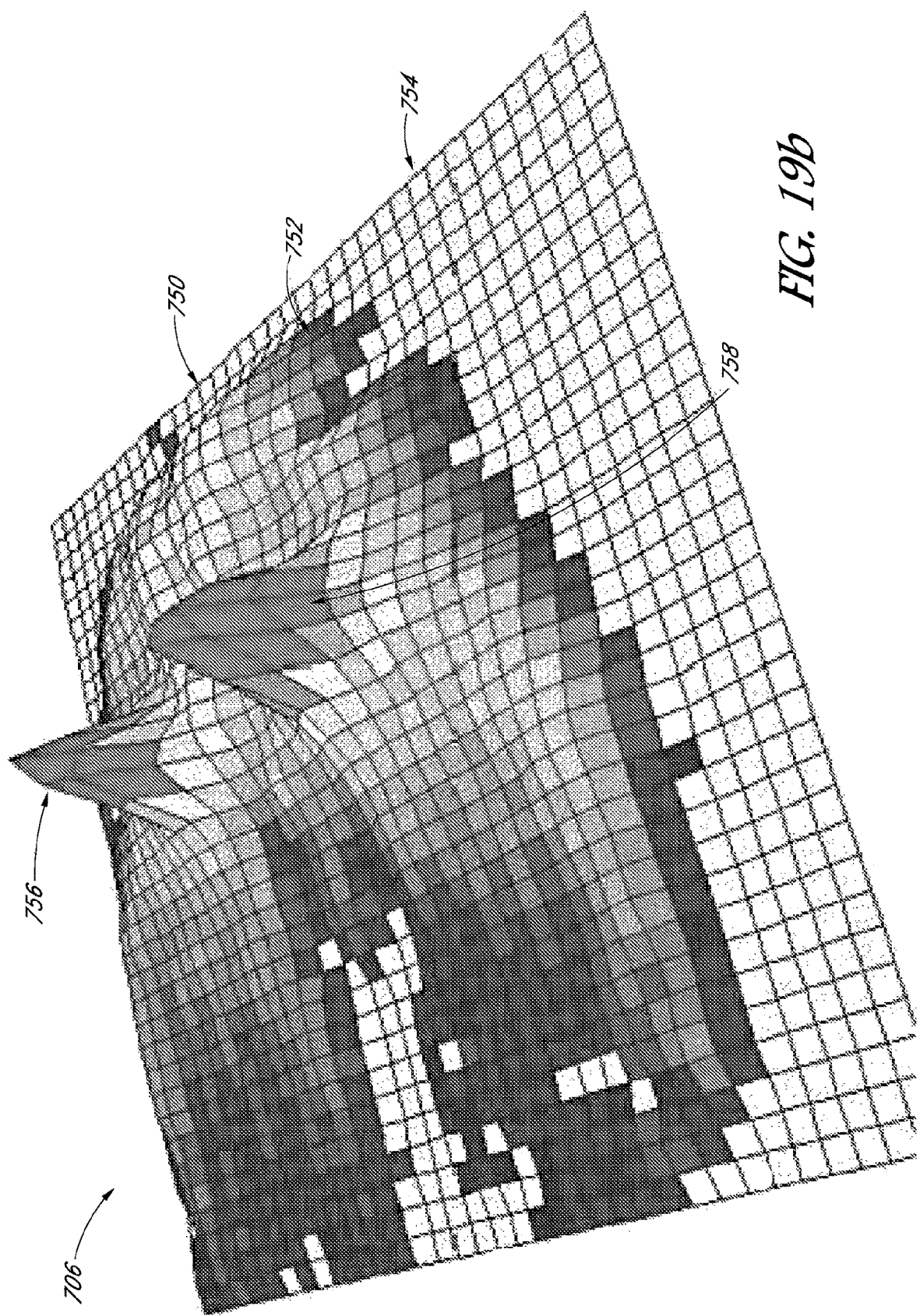
FIG. 19b is a schematic illustration of another optional graphical representation of force including a three-dimensional force map.

FIG. 19b illustrates yet another optional format for the display of force information. In the embodiment of FIG. 19b, the display device 706 is configured to generate a three dimensional map 750 including a graphical representation of force data 752 corresponding to the output of sensors. For example, the map 750 can include a plane 754 corresponding to a zero force, and positive force values can be represented as extending upwardly, normal to the plane 754. In the illustrated embodiment of FIG. 19b, two maximum pressure locations 756, 758 are illustrated as two peaks on the three dimensional map. These representations 756, 758 can be considered to be exaggerated examples of displayed force information that could correspond to the output of sensors corresponding to the representations 720, 724, described above.

Figure 19C:
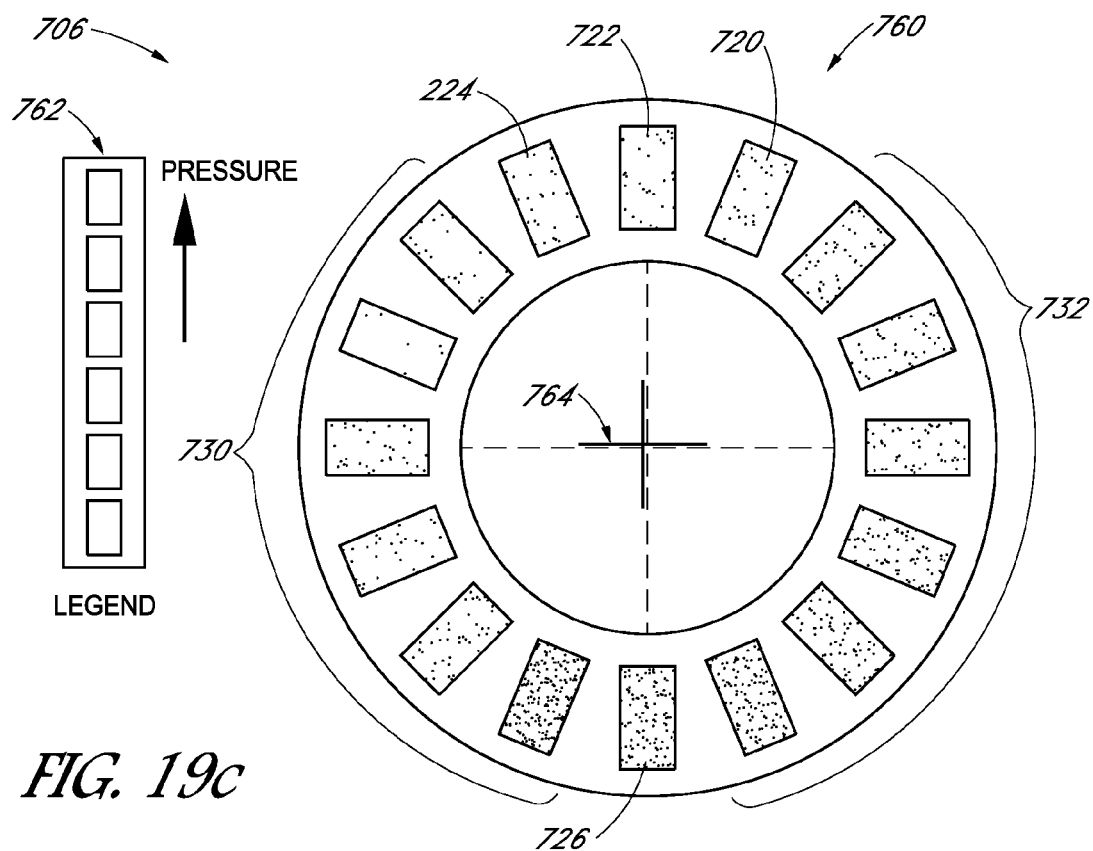
FIG. 19c is schematic illustration of another optional format for representing force information on a user interface, including a circular arrangement of pressure readings, optionally color coded and with an optional reticle-style balance visualizer.
Figure 19D:
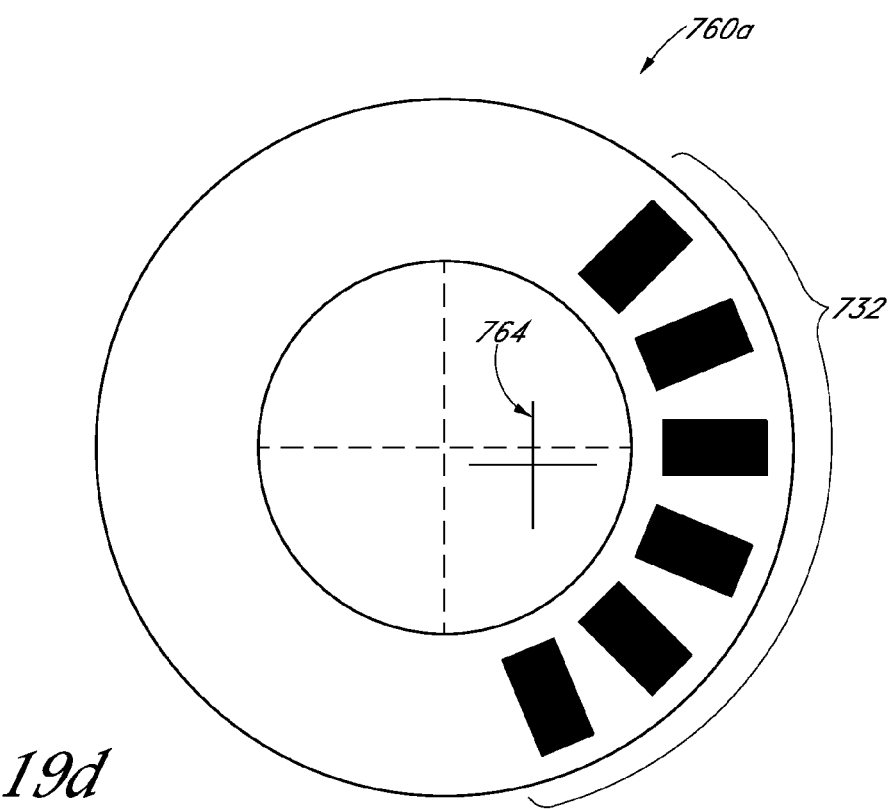
FIG. 19d is a schematic representation of a modification of the format of FIG. 19c, including selective presentations of pressure readings and a movable reticle representing force balance.

With reference to FIG. 19c, the display 706 can be configured to display force data in a radial pattern, schematically corresponding to the layout of sensor representations 720-732 described above with reference to FIGS. 18 and 19a. In the optional format of FIG. 19c, the display 706 displays the force data in the form of a radial, color coded graphical representation in the form of a radial pattern 760. For example, the radial format 760 can include a legend 762 providing a color gradation corresponding to a range of forces or pressures. Additionally, the display 706 can be configured to color code geometric shapes around the radial format 760 with the geometric shapes, such as rectangles, filled in with colors corresponding to the legend 762. Additionally, the radial format 760 can include a reticle 764 which can be represented in a position within the radial format 760 indicating a balance point. For example, the reticle 764 can be in the form of a cross. When the reticle 764 is represented in the center of the radial format 760, such a position would indicate that the pressures represented around the periphery of the radial format 760 are roughly in balance with each other. However, if higher pressures or forces are detected on one side of the associated mask, the reticle 764 can be displayed in an off center location. As such, the reticle 764 can provide guidance for a user for rebalancing the forces around the mask.

With reference to FIG. 19, a modification of the radial format 760 is illustrated therein and identified generally by the reference numeral 760a. In the format 760a of FIG. 19b, force data can be selectively represented in a more emphasized way to illustrate imbalance. For example, as shown in FIG. 19d, some of the values associated with the plurality of positions of representation 732 are represented with colored blocks. Additionally, the reticle 764 is presented in a location offset from center, positioned closer to the plurality of positions of representation 732. Thus, a user can interpret this representation as indicating that there is excessive force on the portion of the mask 200 corresponding to the sensor location 732. Thus, if the user adjusts the associated mask 200 so as to achieve more balanced forces around the periphery of the mask, the reticle 764 can be moved towards the center of the radial format 760a, and the display of the selected blocks within the plurality of position 732 can be deleted.

Figure 19E:
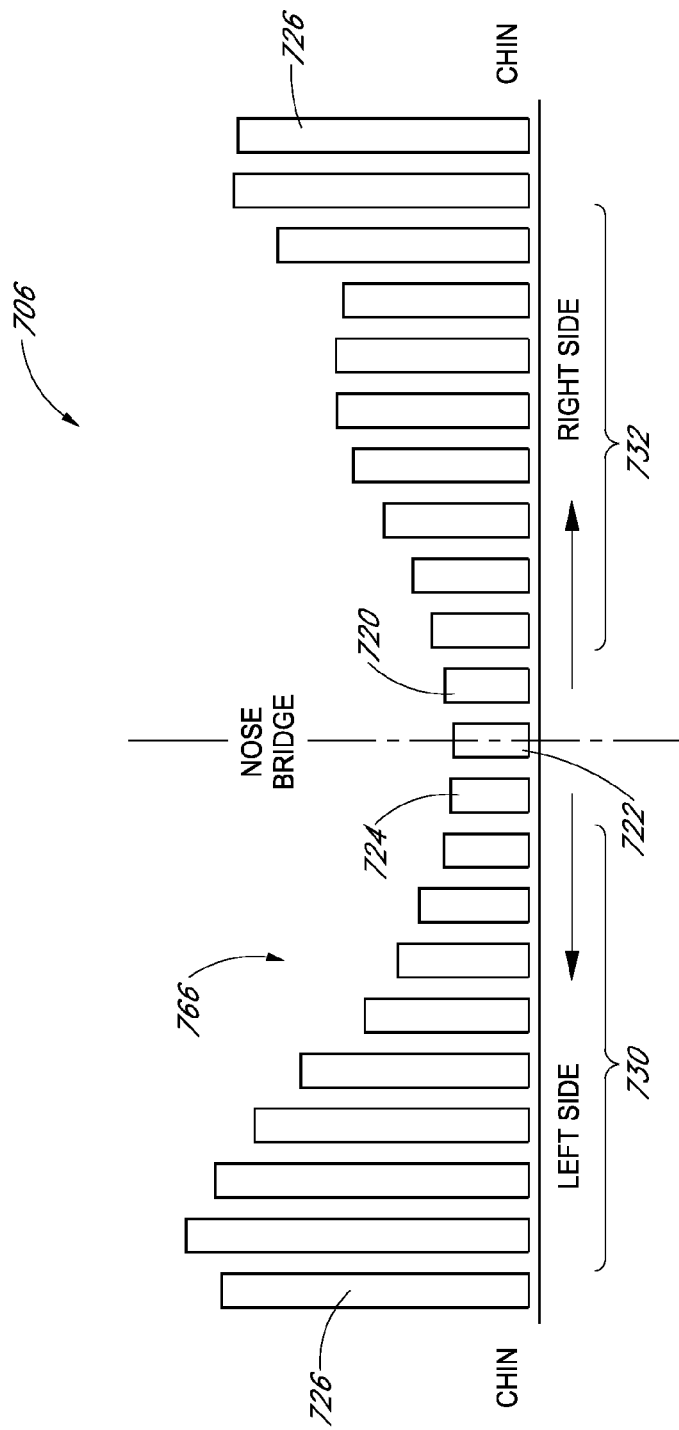
FIG. 19e is schematic illustration of another optional format for representing force data including a horizontally extending bar graph having a pressure value associated with the nose bridge in the center and with the left and right adjacent sensor readings extending toward the left and right, respectively.

FIG. 19e illustrates an optional horizontal bar graph display format 766. In this optional display format 766, force information is represented as vertically extending bar graphs, with the sensor representations 720, 722, 724 represented in approximately the center of the graph, the left side plurality at representation 730 is displayed on the left side of the graph and the right side plurality at representation 732 is disposed on the right side of the graph, and the chin location representation 726 plotted optionally on both the left and the right ends of the bar graph. As such, the format 766 provides another optional format for illustrating the balance of forces around the periphery of a mask.

Figure 19G:
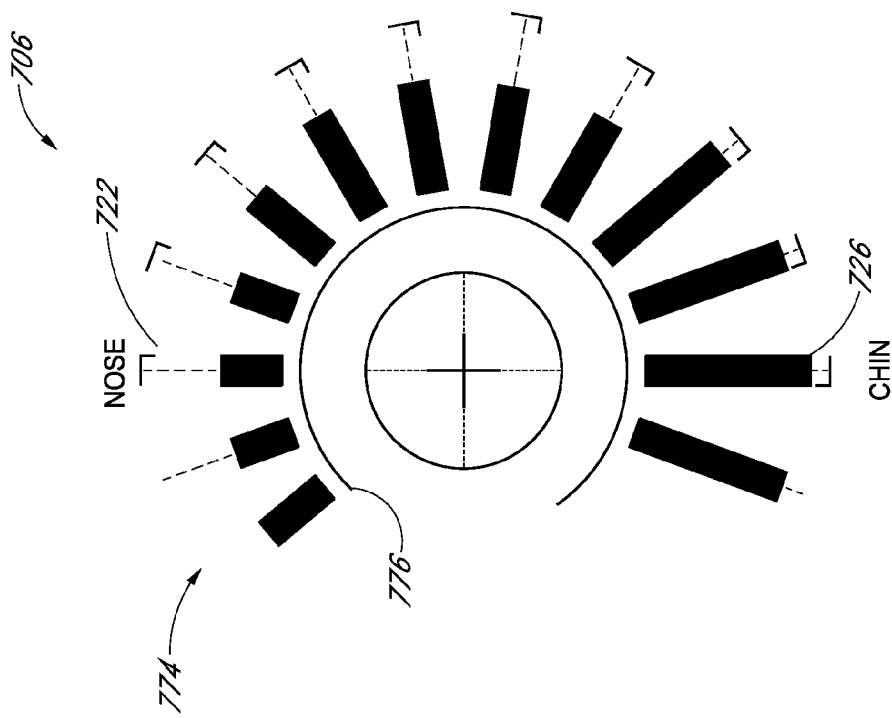
FIG. 19g is another optional format for representing force data in the form of a circular arrangement with force magnitudes represented on radially varying bar graphs.
Figure 19F:
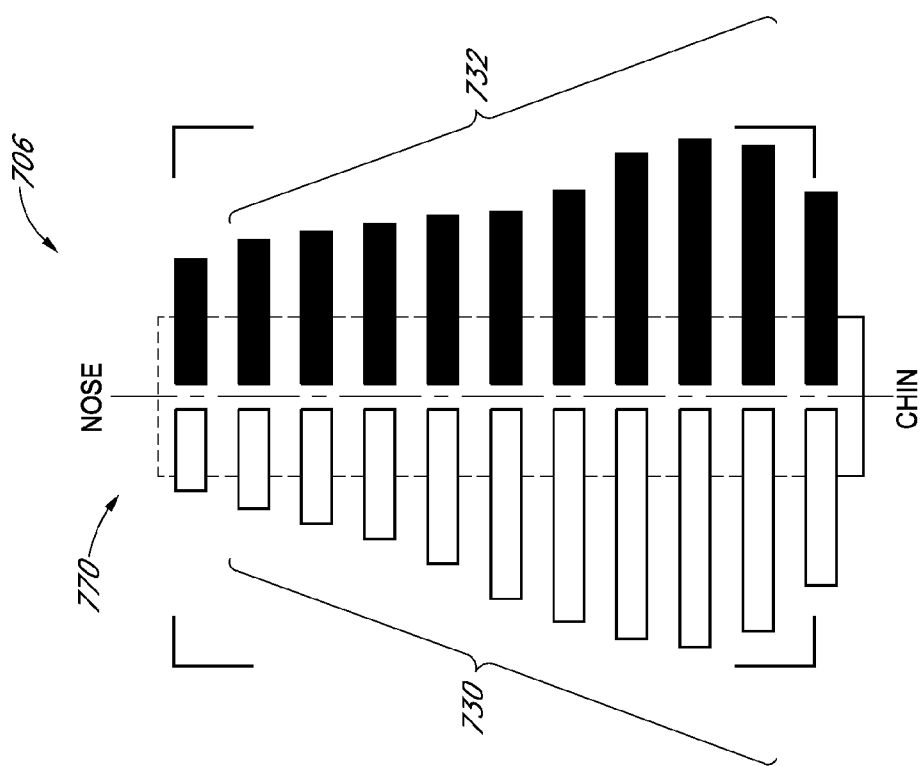
FIG. 19f is another optional format for representing force data including left and right pluralities of force representations arranged in two parallel, vertical groupings, with the forces proximate to the nose at the top and forces proximate to the chin at the bottom.

FIG. 19f illustrates another optional display format 770, in the form of a vertically split bar graph. In the illustrated embodiment format 770, the left side plurality of sensor representation 730 are displayed in the form of variable length bars extending from the center of the format 770 to the left and the right side plurality at representation 732 are displayed as horizontal bars extending from the center of the format 770, towards the right. Optionally, the bars associated with the location of representations 730, 732, as well as the other sensor locations, can be color coded. In one example of the display in the format 770, the right side plurality at representation 732 are displayed in a different color than that used for displaying the location of representation 730, thereby indicating excessive force on the right side of the mask 200. A user can thus use such a display to reduce the pressure on the right side or increase the pressure on the left side of an associated mask 200 to thereby achieve a more balanced fitment.

FIG. 19g illustrates another variation of a radial layout, identified by the reference numeral 774. In the format 774, force data is represented in radial bars, extending from the inner ends of the bars which follow and enter periphery 776. Increase in pressures are displayed as corresponding to individual bars having an increasing radial length. For example, in the embodiment of FIG. 19g, the bars associated with the sensor representation 726, proximate to a user's chin, are illustrated as detecting a higher force than the sensor at representation 722 associated with a position proximate to a user's nose bridge. As noted above, the various different formats can incorporate color coding, three dimensional shapes, or bar lengths so as to graphically illustrate the detected forces and also to provide prompts to a user for achieving a better fit of an associated mask.

Figure 20:
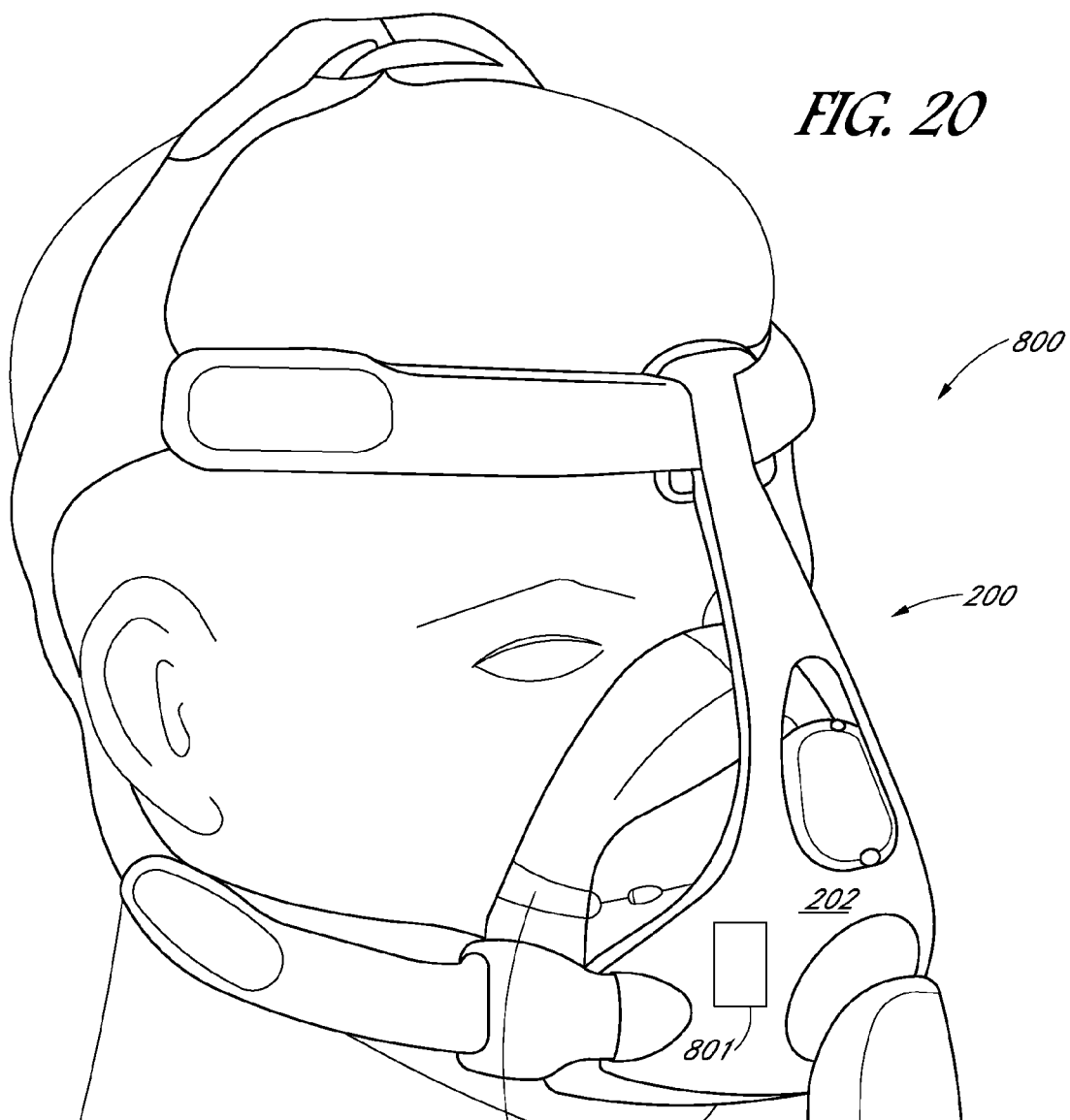
FIG. 20 is a perspective view of another modification of the fluid delivery device including a display device.
Figure 21:
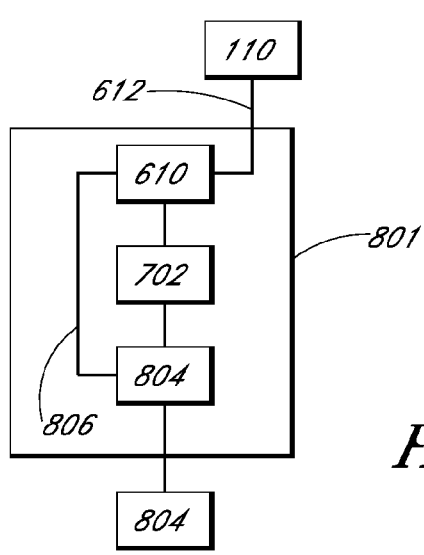
FIG. 21 is a schematic diagram of the fluid delivery device of FIG. 20 with an included display device.

FIG. 20 illustrates yet another embodiment of a mask fitment system, identified generally by the reference numeral 800. The fitment system 800 includes a display device, such as LEDs 802 disposed on the mask, in this embodiment, the mask 200, however, it is to be understood that the mask fitment system 800 can comprise any of the masks described above.

The fitment system 800 can include a sensor and display driver 801 disposed anywhere on the mask 200, for example, on the frame portion 202.

Figure 22:
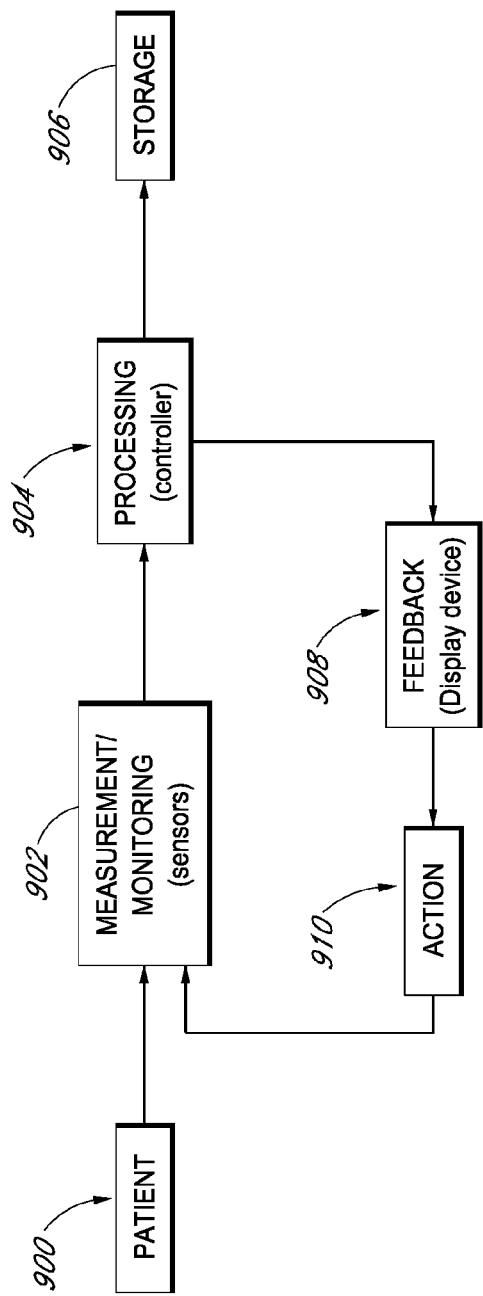
FIG. 22 is a flow chart illustrating an optional method for using any of the masks described above.

As shown in FIG. 22, the sensor and display driver 801 can include the sensor driver 610, described above, and a power supply 702 connected to the driver 610. Additionally, the sensor and display driver 804 can include a display driver unit 804.

The display driver unit 804 can be configured to receive the output of the driver 610 either by serial lead 806 or by wireless signal. The display driver 804 can include math processing circuitry or software configured to convert the signals received from the driver 610 into a light driver signal, such as an LED light driver signal.

The output from the display driver 804 can be connected to one or a plurality of LEDs 802. For example, with or without limitation, the LEDs 802 can be in the form of RGB LED lights. Additionally, the display driver 804 can be in the form of an RGB LED light driver. Additionally, the display driver 804 can include circuitry or programming to output a signal to the LEDs 802 so as to change the color of the light output from the LEDs 802 in a predetermined proportional relationship to the signals received from the driver 610. For example, values indicative of low forces received by the driver 804 can be converted into light blue color signals delivered to the LEDs 802, thereby causing the LEDs 802 to emit a light blue color. On the other hand, the driver 804 can be configured to output red light signals to the LEDs 802 in response to signals from the driver 610 indicative of high forces. As such, during operation, when a healthcare worker is looking at a patient wearing the mask 200, the healthcare workers will see red lights in areas where higher pressures are detected and blue lights in the areas where lower pressures are detected. The healthcare worker can then adjust the mask 200 in order to achieve a uniform pressure around the mask 200 with the lowest magnitude of forces and an acceptable leak rate. Additionally, if a patient attempted to fit the mask on themselves, by looking in a mirror, they would also see colors of lights in the correct orientation to understand how to adjust the mask.

FIG. 22 illustrates a method that can be employed using any of the masks or fitment systems described above, although for brevity, the following description refers to one or both of the fluid delivery device 100 and the mask 200 in the descriptions of some examples. In the flow chart of FIG. 23, the method begins at operation block 900. In the operation block 900, a fluid delivery device, such as a mask 200, or any of the other masks disclosed herein, can be fit onto a patient. After the operation block 900, the method can proceed to operation block 902.

In the operation block 902, forces can be detected at one or more locations where the fluid delivery device contacts the patient. For example, any of the arrangements, layouts, or configurations of the sensor 500 on any of the masks described above can be used to detect forces, which may be indicative of forces imparted onto an area of the patient AS (FIG. 3). After the operation block 902, the method can proceed to operation block 904.

In the operation block 904, the outputs from the sensors can be processed. For example, outputs from any of the sensors described above can be input to an appropriate driver, such as the driver 610 (FIGS. 16 and 17). Additionally, the output from the sensors can be converted to output such as data having a predetermined relationship to the forces detected by the sensors in operation block 902. For example, the driver 610 can be configured to receive output from the sensors 500 and output one or more signals representative of the capacitance of the sensors where the sensors are capacitive sensors. Optionally, in operation block 904, the output of the sensors can be further processed into the desired units such as force units, pressure units, load units, or other units. Further, optionally, in the operation block 904, the output from the sensors can be further converted into data that can be used by a display device for presenting representations of the forces detected by the sensors. After the operation block 904, the method can move on to operation block 906.

In the operation block 906, data based on the output from the sensors can be stored. For example, the data generated in operation block 904 can be stored continuously, in batches, selectively, sampled at intervals, or any other desired storage technique.

Additionally, the method can continue from operation block 904 to operation block 908.

In the operation block 908, data generated in the operation block 904 can be displayed to a user. For example, the data generated in operation block 904 can be displayed on a graphical monitor, a mobile computing device, or any other type of device. Additionally, for example, the data generated in operation block 904 can be presented in the formats represented in FIG. 18 or 19*a-g*, or any other desired format. Additionally, the display device used in operation block 908 can be configured to present a user interface allowing a user to select the options of representing the data in the formats of FIG. 18 or 19*a-g* or any other format. After the operation block 908, the method can move to operation block 910.

In the operation block 910, a user, including the patient or a clinician such as a nurse or sleep technician, can take responsive action to the information output in operation block 908. For example, if the information displayed in the operation block 908 indicates uneven or excessive pressure on a portion of the mask, the user can adjust the mask with the goal of reducing pressure, reducing the magnitude of pressure force differentials, and achieving an acceptable leak rate. Adjustment of the mask 200 can include adjustment of the orientation of the straps of the strap arrangement 212 and/or other adjustments of the frame portion 202 and/or seal portion 204. After the operation block 910, the method can return to operation block 902 and repeat until the desired fitment is achieved.

With continued reference to FIGS. 3, 16, and 17, after the desired fitment of the fluid delivery device 100 is achieved, the use of the fluid delivery device 100 can continue with the delivery of a therapeutic fluid from the therapeutic fluid delivery supply 602, through the conduit 108, to the target area R.

Optionally, execution of any combination of the operations of operation blocks 902, 904, 906, 908, 910 can repeat and continue during the delivery of a therapeutic fluid. As such, the care of the patient can include and benefit from the data output from the one or more sensors 110 on the fluid delivery device 100, or the processing of that data, to further improve patient comfort and leak management. Additionally, data stored in operation block 906 can be used to identify causes of inadvertent injuries or non-optimal effectiveness of the therapy. For example, if a patient receives therapy for long periods of time such as CPAP therapy while sleeping or unconscious or non-lucid patients receive NIV therapy, stored pressure data (collected in operation block 906) may reflect changes in forces at the sealing surface 105 consistent with the appearance of an injury, perceived discomfort, or non-optimal effectiveness of the therapy.

A number of examples of therapeutic fluid delivery device aspects of the interfaces, and variations on each aspect, have been discussed with reference to other Figures. The present application contemplates that a therapeutic fluid delivery device may incorporate some aspects but not other aspects. For example, a therapeutic fluid delivery device might incorporate aspects of a mask while using a different arrangement for securing the mask to the user. All of these variations are considered within the scope of this application.

Although the present inventions are disclosed in terms of certain embodiments, other embodiments apparent to those of ordinary skill in the art also are within the scope of these inventions. Thus, various changes and modifications may be made without departing from the spirit and scope of the inventions. For instance, various components may be repositioned as desired. Moreover, not all of the features, aspects and advantages are necessarily required to practice the present inventions. Accordingly, the scope of the present invention is intended to be defined only by claims herein or claims submitted at a future date.

What is claimed is:

1. A respiratory mask comprising:
a seal portion comprising a sealing surface configured to form a seal with a patient's face;
a plurality of elastic sensors are configured to detect a force applied to the seal portion,
wherein the plurality of elastic sensors comprise layered capacitive sensors, and
wherein the plurality of elastic sensors comprise a first longitudinal layer including a first electrode and second and third transverse layers including second and third electrodes overlapping the first electrode, wherein the first and second electrodes from a first capacitive sensor and the first and third electrodes form a second capacitive sensor; and
a controller configured to receive from a user a predetermined minimum leak rate and a predetermined maximum sealing force,
wherein the controller is configured to determine whether the force applied to the seal portion exceeds the predetermined maximum sealing force while the respiratory mask is achieving the predetermined minimum leak rate, and
wherein the controller indicates to the user that a different respiratory mask should be considered for the patient's face when the force applied to the seal portion exceeds the predetermined maximum sealing force.

2. The respiratory mask of claim 1, wherein the plurality of elastic sensors comprise a first sensor configured to detect a force at a first location on the seal, and a second sensor configured to detect a force at a second location on the seal portion different than the first location.

3. The respiratory mask of claim 1, wherein the plurality of elastic sensors are configured to detect forces applied by the sealing surface to at least one of a portion of the patient's face or head.

4. The respiratory mask of claim 1, wherein the seal portion further comprises a cushion, the plurality of elastic sensors are configured to detect compression of the cushion.

5. The respiratory mask of claim 1, wherein the plurality of elastic sensors are configured to output signals indicative of force applied to the seal portion.

6. The respiratory mask of claim 1, wherein the plurality of elastic sensors are configured to deform and to output signals in response to deformation.

7. The respiratory mask of claim 1, further comprising a recording device configured to store output from at least elastic sensors.

8. The respiratory mask of claim 1, further comprising a frame portion, the seal portion being mounted to the frame portion, wherein at least one of the plurality of elastic sensors are disposed between the seal portion and the frame portion.

9. The respiratory mask of claim 1, wherein the plurality of elastic sensors comprise a first row of force sensors extending along a longitudinal direction of the seal portion and a second row of force sensors extending parallel to the first row.

10. The respiratory mask of claim 1, wherein at least a first of the plurality of elastic sensors comprises first and second electrodes spaced apart by a dielectric layer, the first electrode comprising conductive silicone.

11. The respiratory mask of claim 1, wherein at least a first of the plurality of elastic sensors comprises first and second electrodes spaced apart by a dielectric layer, the dielectric layer comprising silicone.

12. A respiratory mask comprising:
a seal portion comprising a sealing surface configured to form a seal with a patient's face;
at least one elastic sensor configured to detect a force applied to the seal portion;
a controller configured to receive from a user a predetermined minimum leak rate and a predetermined maximum sealing force,
wherein the controller is configured to determine whether the force applied to the seal portion exceeds the predetermined maximum sealing force while the respiratory mask is achieving the predetermined minimum leak rate, and
wherein the controller indicates to the user that a different respiratory mask should be considered for the patient's face when the force applied to the seal portion exceeds the predetermined maximum sealing force; and
wherein the at least one elastic sensor is a layered capacitive sensor comprising a plurality of layers of electrodes with a dielectric layer disposed between each of the plurality of layers of electrodes, such that the at least one elastic sensor comprises a plurality of capacitors in a configuration in which they share at least one electrode.

13. The respiratory mask of claim 12, wherein the at least one elastic sensor comprises a dielectric layer on an outer surface of the at least one elastic sensor.

14. The respiratory mask of claim 12, wherein the layered capacitive sensor comprises a longitudinal unit and a transverse unit, wherein the longitudinal unit comprises a lower electrode and a dielectric layer, and wherein the transverse unit comprises an upper electrode.

15. The respiratory mask of claim 14, wherein the at least one elastic sensor comprises a plurality of transverse units, and wherein the longitudinal unit provides a common electrode for each of the plurality of capacitors of the at least one elastic sensor.

16. The respiratory mask of claim 12, wherein at least one of the plurality of capacitors comprise a lower electrode, an upper electrode, and a dielectric layer disposed between the lower electrode and the upper electrode, wherein the lower electrode provides a common electrode for each of the plurality of capacitors.

17. The respiratory mask of claim 12, wherein one of the at least one elastic sensor comprises conductive silicone.

18. The respiratory mask of claim 12, wherein the dielectric layer comprises silicone.

19. The respiratory mask of claim 12, wherein at least one of the at least one elastic sensor comprises first and second electrodes spaced apart by the dielectric layer, wherein at least one of the dielectric layer and the first and second electrodes comprises silicone, and wherein the seal portion comprises silicone.

20. The respiratory mask of claim 12, further comprising a dielectric outer layer for encapsulation.

21. A respiratory mask comprising:
- a seal portion comprising a sealing surface configured to form a seal with a patient's face;
- a plurality of elastic sensors configured to detect a force applied to the seal portion; and
- a controller configured to receive from a user a predetermined minimum leak rate and a predetermined maximum sealing force,
    - wherein the controller is configured to determine whether the force applied to the seal portion exceeds the predetermined maximum sealing force while the respiratory mask is achieving the predetermined minimum leak rate, and
- wherein the controller indicates to the user that a different respiratory mask should be considered for the patient's face when the force applied to the seal portion exceeds the predetermined maximum sealing force.

* * * * *